US006245769B1

(12) United States Patent
Arvanitis et al.

(10) Patent No.: US 6,245,769 B1
(45) Date of Patent: *Jun. 12, 2001

(54) HETEROCYCLYL-SUBSTITUTED RING-FUSED PYRIDINES AND PYRIMIDINES AS CORTICOTROPIN RELEASING HORMONE (CRH) ANTAGONISTS, USEFUL FOR TREATING CNS AND STRESS-RELATED DISORDERS

(75) Inventors: Argyrios G. Arvanitis, Kennett Square, PA (US); Paul J. Gilligan, Wilmington, DE (US); James P. Beck, Smyrna, DE (US); Rajagopal Bakthavatchalam, Wilmington, DE (US)

(73) Assignee: DuPont Pharmaceuticals Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/145,231

(22) Filed: Sep. 1, 1998

Related U.S. Application Data
(60) Provisional application No. 60/057,432, filed on Sep. 2, 1997.

(51) Int. Cl.$^7$ .................. A61K 31/4192; A61K 31/519; C07D 403/04
(52) U.S. Cl. .................. 514/258; 514/261; 514/300; 514/301; 514/302; 514/303; 514/299; 544/183; 544/184; 544/212; 544/254; 544/262; 544/263; 544/264; 544/277; 544/349; 544/350; 546/112; 546/113; 546/114; 546/115; 546/117; 546/118; 546/119
(58) Field of Search .................. 514/255, 258, 514/261, 300, 301, 302, 303, 299; 544/183, 184, 212, 254, 262, 263, 264, 277, 349, 350; 546/112, 113, 114, 115, 117, 118, 119

(56) References Cited

U.S. PATENT DOCUMENTS
5,378,700 * 1/1995 Sakuma et al. ................. 514/212

FOREIGN PATENT DOCUMENTS
| | | |
|---|---|---|
| 2011222 | 3/1990 | (CA) . |
| 0706795A2 | 4/1996 | (EP) . |
| 706795 * | 4/1996 | (EP) . |
| 0778277A1 | 6/1997 | (EP) . |
| 9411050 | 5/1994 | (WO) . |
| 9533727 | 12/1995 | (WO) . |
| 9533750 | 12/1995 | (WO) . |
| 9534563 | 12/1995 | (WO) . |
| 9640142 | 12/1996 | (WO) . |
| WO 96/40142 * | 12/1996 | (WO) . |
| WO 97/27199 * | 7/1997 | (WO) . |
| 9727199 | 7/1997 | (WO) . |

OTHER PUBLICATIONS

Gold et al., *Responses to Corticotropin–Releasing Hormone in the Hypercortisolism of Depression and Cushing's Disease*, May 1986, pp. 1329–1335.

Morley et al., *Neuropeptides: Conductors of the Immune Orchestra*, 1987, pp. 527–544.

Vale et al., *Characterization of a 41–Residue Ovine Hypothalamic Peptide that Stimulates Secretion of Corticotropin and β–Endorphin*, 1981, pp. 1394–1397.

Britton et al., *Corticotropin Releasing Factor and Amphetamine Exaggerate Partial Agonist Properties of Benzodiazepine Antagonist Ro 15–1788 in the Conflict Test*, 1988, pp. 306–311.

Swerdlow et al., *Corticotropin–Releasing Factor Potentiates Acoustic Startle in Rats: Blockade by Chloridazepoxide*, 1986, pp. 147–152.

Britton et al, *Chlordiazepoxide Attenuates Response Suppression Induced by Corticotropin–Releasing Factor in the Conflict Test*, 1985, pp. 170–174.

Dunn et al., *Physiological and Behavioral Responses to Corticotropin–Releasing Factor Administration: Is CRF a Mediator of Anxiety or Stress Responses?*, 1990, pp. 71–100.

Berridge et al, *A Corticotropin–Releasing Factor Antagonist Reverses the Stress–Induced Changes of Exploratory Behavior in Mice*, 1987, pp. 393–401.

(List continued on next page.)

Primary Examiner—Richard L. Raymond
Assistant Examiner—Deepak R. Rao
(74) Attorney, Agent, or Firm—Maureen P. O'Brien; Kalim S. Fuzail

(57) ABSTRACT

Corticotropin releasing factor (CRF) antagonists of Formula (I):

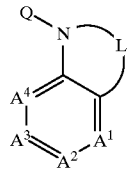

and their use in treating psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

15 Claims, No Drawings

OTHER PUBLICATIONS

Berridge et al., *Corticotropin–Releasing Factor Elicits Naloxone Sensitive Stress–Like Alterations in Exploratory Behavior in Mice*, 1986, pp. 83–93.

Grigoriadis et al., *Effects of Chronic Antidepressant and Benzodiazepine Treatment on Corticotropin–Releasing–Factor Receptors in Rat Brain and Pituitary*, 1989, pp. 53–60.

Britton et al., *Intraventricular Corticotropin–Releasing Factor Enhances Behavioral Effects of Novelty*, 1982, pp. 363–367.

Saplosky, Robert M., *Hypercortisolism Among Socially Subordinate Wild Baboons Originates at the CNS Level*, Nov. 1989, pp. 1047–1051.

Gold et al., *Psychiatric Implications of Basic and Clinical Studies with Corticotropin–Releasing Factor*, May 1984, pp. 619–627.

Holsboer et al., *ACTH and Multisteroid Responses to Corticotropin–Releasing Factor in Depressive Illness: Relationship to Multisteroid Responses After ACTH Stimulation and Dexamethasone Suppression*, 1983, pp. 147–160.

Nemeroff et al., *Reduced Corticotropin Releasing Factor Binding Sites in the Frontal Cortex of Suicide Victims*, Jun. 1988, pp. 577–579.

Banki et al., *CSF Corticotropin–Releasing Factor–Like Immunoreactivity in Depression and Schizophrenia*, Jul. 1987, pp. 873–877.

Nemeroff et al., *Elevated Concentrations of CSF Corticotropin–Releasing Factor–Like Immunoreactivity in Depressed Patients*, 1984, pp. 1342–1344.

Blalock, J. Edwin, *A Molecular Basis for Bidirectional Communication Between the Immune and Neuroendocrine Systems*, Jan. 1989, pp. 1–32.

Koob, George F., *Stress, Corticotropin–Releasing Factor, and Behavior*, 1985, pp. 39–52.

Rivier et al., *Characterization of Rat Hypothalamic Corticotropin–Releasing Factor*, Aug. 1983, pp. 4851–4855.

DeSouza, Errol B., *CRH Defects in Alzheimer's and Other Neurologic Diseases*, Sep. 1988, pp. 59–71.

Vale et al, *Chemical and Biological Characterization of Corticotropin Releasing Factor*, 1983, pp. 245–271.

DeSouza et al., *Corticotropin–Releasing Factor Receptors are Widely Distributed Within the Rat Central Nervous System: An Autoradiographic Study*.

Haidoune et al., Chem. Abstract 122: 188009, 1995.*

Lettre et al., Chem. Abstract 55: 22324f, 1962.*

* cited by examiner

US 6,245,769 B1

HETEROCYCLYL-SUBSTITUTED RING-FUSED PYRIDINES AND PYRIMIDINES AS CORTICOTROPIN RELEASING HORMONE (CRH) ANTAGONISTS, USEFUL FOR TREATING CNS AND STRESS-RELATED DISORDERS

This application claims the benefit of U.S. Provisional Application No. 60/057,432, filed Sep. 2, 1997.

FIELD OF THE INVENTION

The present invention relates to novel compounds, pharmaceutical compositions, and methods for the treatment of psychiatric disorders and neurological diseases, including major depression, anxiety-related disorders, post-traumatic stress disorder, supranuclear palsy and feeding disorders, as well as treatment of immunological, cardiovascular or heart-related diseases and colonic hypersensitivity associated with psychopathological disturbance and stress. In particular, the present invention relates to novel heterocyclyl-substituted ring-fused pyridine and pyrimidine compounds, pharmaceutical compositions containing such compounds and methods of use in treating psychiatric disorders, neurological diseases, immunological, cardiovascular or heart-related diseases and colonic hypersensitivity associated with psychopathological disturbance and stress, by administration of the compounds of the invention.

BACKGROUND OF THE INVENTION

Corticotropin releasing factor (herein referred to as CRF), a 41 amino acid peptide, is the primary physiological regulator of proopiomelanocortin(POMC)—derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebral spinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the ganxiogenicm effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist ($\alpha$-helical CRF$_9$-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

Several publications describe corticotropin releasing factor antagonist compounds and their use to treat psychiatric disorders and neurological diseases. Examples of such publications include DuPont Merck PCT application US94/11050, Pfizer WO 95/33750, Pfizer WO 95/34563, Pfizer WO 95/33727 and Pfizer EP 0778 277 A1.

PCT Patent Application WO 96/40142 discloses compounds useful in treatment of hyperproliferative diseases such as cancers and acnes, having the general formula shown below,

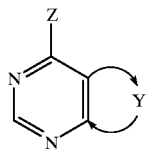

wherein Z is NR$^1$R$^2$ and R$^1$ is H and R$^2$ is phenyl substituted by (R$^5$)m or Q or R$^1$R$^2$N is a group of the formula

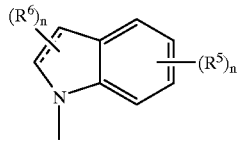

PCT Patent Application WO 97/27199-A discloses 7H-pyrrolo[2,3-d]pyrimidine derivatives which are useful in treatment of cardiovascular disease, cerebrovascular disease and renal disease.

EP Patent Application EP0706795 discloses catechol diether compounds as inhibitors of tumor necrosis fact release, having the general formula shown below

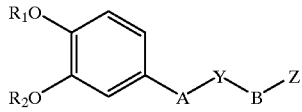

wherein Z can be benzimidazole substituted with quinoline. However, compounds of this type are not included in the compounds of the present invention.

U.S. Pat. No. 5,378,700 discloses fused pyrimidine derivatives useful for treatment of hypoxemia associated with respiratory diseases, having the general formula shown below

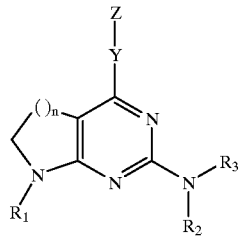

wherein Y and Z together represent a fused biheterocyclic ring which has 1–3 N in any position being bonded via the N-atom to the 4-position of the pyrimidine. However, compounds of this type are not included in the compounds of the present invention.

CA Patent No. 2,011,222 discloses benzimidazole and azabenzimi-dazole derivatives useful for treatment of cardiovascular diseases and duodenal ulcers, having the general formula shown below

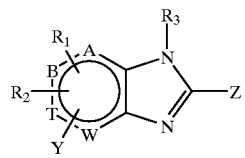

wherein Y can be benzimidazole and Z can be phenyl or pyridyl. However, those compounds are not included in the compounds of the invention.

Insofar as is known, novel triazolopyridines and pyrimidines, which are described in detail below, have not been previously reported as corticotropin releasing factor antagonist compounds useful in the treatment of psychiatric disorders and neurological disease, including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress.

SUMMARY OF THE INVENTION

In accordance with one aspect, the present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in mammals.

According to another aspect, the present invention provides novel compounds of formula (I) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of formula (I), and methods of using such compounds for the suppression of CRF hypersecretion, and/or for the treatment of anxiogenic disorders.

According to yet another aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV)

infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.a., dependencies on alcohol, cocaine, heroin, benzodiazepines, or other drugs); drug and alcohol withdrawal symptoms; osteoporosis; psychosocial dwarfism and hypoglycemia in mammals.

According to a still further aspect of the invention, the compounds provided by this invention (and especially labelled compounds of this invention) are also useful as standards and reagents in determining the ability of a potential pharmaceutical to bind to the CRF receptor.

DETAILED DESCRIPTION OF THE INVENTION

[1] Thus, in a first embodiment, the present invention provides a novel compound of formula I:

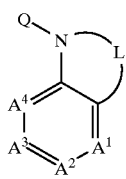

(I)

and isomers thereof, stereoisomeric forms thereof, or mixtures of stereoisomeric forms thereof, and pharmaceutically acceptable salt forms thereof wherein:

Q is selected from the group consisting of:

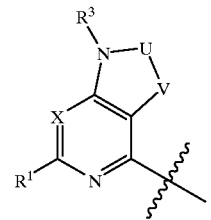

Ia

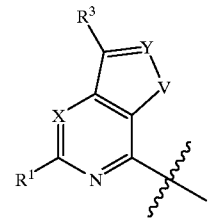

Ib

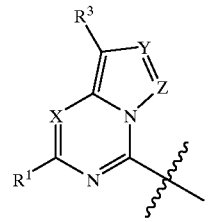

Ic

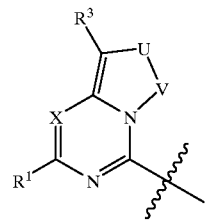

IIa

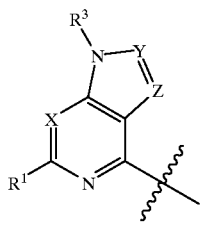

IIb

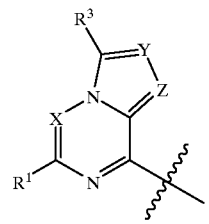

IIc

X is N or $CR^1$;
Y, Z are independently N or $CR^2$;
U, V are independently >C=G, $CR^{13}R^{14}$, or $NR^{13}$, O, or S without forming O—O, S—O, or S—S bonds;
G is O or S;
$R^1$ is independently at each occurrence —H, halogen, —CN, $C_1$–$C_4$ haloalkyl, —$NR^9R^{10}$, —$NR^9COR^9$, —$COR^{10}$, —$OR^{10}$, SH or —$S(O)_nR^{12}$, $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, where each $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl is each optionally substituted with halogen, —CN, $C_1$–$C_4$ haloalkyl, —$NR^9R^{10}$, —$NR^9COR^9$, —$COR^{10}$, —$OR^{10}$, SH or —$S(O)_nR^{12}$;
$R^2$ is —H, halogen, —CN, $C_1$–$C_4$ haloalkyl, —$NR^9R^{10}$, —$NR^9COR^9$, —$COR^{10}$, —$OR^{10}$, SH or —$S(O)_nR^{12}$, $C_1$–$C_4$ alkyl, $C_3$–$C_6$ cycloalkyl, $C_3$–$C_7$ cycloalkylalkyl, each optionally substituted with halogen, CN, $C_1$–$C_4$ haloalkyl, —NR$^9$R$^{10}$, NR$^9$COR$^9$, —COR$^{10}$, —OR$^{10}$, SH or —S(O)$_n$R$^{12}$;

R$^3$ is C$_1$–C$_{10}$ alkyl, C$_2$–C$_{10}$ alkenyl, C$_2$–C$_{10}$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, C$_5$–C$_{10}$ cycloalkenylalkyl, where one carbon in any cycloalkyl ring may be replaced with O, S or NR$^9$ and each C$_1$–C$_{10}$ alkyl, C$_2$–C$_{10}$ alkenyl, C$_2$–C$_8$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, C$_5$–C$_{10}$ cycloalkenylalkyl is optionally substituted with 1 to 3 substituents independently selected at each occurrence from C$_1$–C$_6$ alkyl, C$_2$–C$_6$ alkenyl, C$_2$–C$_{10}$ alkynyl, C$_3$–C$_6$ cycloalkyl, halogen, C$_1$–C$_4$ haloalkyl, cyano, —OR$^7$, SH, —S(O)$_n$R$^{11}$, —COR$^6$, —NHR$^6$SO$_2$R$^8$, —OC(O)NR$^6$R$^7$, —N$_3$, —OC(O)OR$^7$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —CONR$^6$R$^7$, —CO$_2$H, aryl, heteroaryl and heterocyclyl or —OR$^{3a}$, —NR$^{3a}$R$^{3b}$, —NHR$^{3a}$, —SO$_n$R$^{3a}$, —SO$_2$NHR$^{3a}$, —SO$_2$NR$^{3a}$R$^{3b}$, —COR$^{3a}$, —CONHR$^{3a}$, —CONR$^{3a}$R$^{3b}$, R$^{3a}$ and R$^{3b}$ are C$_1$–C$_{10}$ alkyl, C$_2$–C$_{10}$ alkenyl, C$_2$–C$_{10}$ alkynyl, C$_3$–C$_8$ cycloalkyl, C$_4$–C$_{12}$ cycloalkylalkyl, C$_2$–C$_{10}$ alkoxyalkyl, C$_5$–C$_{10}$ cycloalkenyl, C$_5$–C$_{10}$ cycloalkenylalkyl, where one carbon in any cycloalkyl may be replaced with O, S or NR$^9$ and each C$_1$–C$_{10}$ alkyl, C$_2$–C$_{10}$ alkenyl, C$_2$–C$_{10}$ alkynyl, C$_3$–C$_8$ cycloalkyl, C$_4$–C$_{12}$ cycloalkylalkyl, C$_2$–C$_1$O alkoxyalkyl, C$_5$–C$_{10}$ cycloalkenyl, C$_5$–C$_{10}$ cycloalkenylalkyl is optionally substituted with 1 to 3 substituents independently selected at each occurrence from C$_1$–C$_6$ alkyl, C$_2$–C$_6$ alkenyl, C$_2$–C$_{10}$ alkynyl, C$_3$–C$_6$ cycloalkyl, halogen, C$_1$–C$_4$ haloalkyl, cyano, —OR$^7$, —SH, —S(O)$_n$R$^{11}$, —COR$^6$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —NHR$^6$SO$_2$R$^8$, —OC(O)NR$^6$R$^7$, —N$_3$, —OC(O)OR$^7$, —CONR$^6$R$^7$, —CO$_2$H, aryl, heteroaryl and heterocyclyl;

L is a two to four atom saturated or partially unsaturated linker group optionally containing one to two B groups and in which one to two carbons of L may be >C=O or >C=S, where L may be substituted with one to three R$^4$ groups;

R$^4$ is independently selected in each occurrence —H, —OR$^{10}$, —COR$^9$, —CO$_2$R$^8$, —CONR$^9$R$^{10}$, —CN, —NR$^9$R$^{10}$, —S(O)$_n$R$^{12}$, halogen, C$_1$–C$_6$ alkyl, C$_1$–C$_4$ haloalkyl, C$_3$–C$_6$ cycloalkyl, C$_2$–C$_6$ alkenyl, C$_2$–C$_6$ alkynyl, aryl or heteroaryl, wherein C$_1$–C$_6$ alkyl, C$_1$–C$_4$ haloalkyl, C$_3$–C$_6$ cycloalkyl, C$_2$–C$_6$ alkenyl, C$_2$–C$_6$ alkynyl, are optionally substituted with the following functional groups: —OR$^{10}$, —COR$^9$, —CO$_2$R$^8$, —CONR$^9$R$^{10}$, —CN, —NR$^9$R$^{10}$, —S(O)$_n$R$^{12}$ halogen;

B is O, S(O)$_n$ or NR$^9$;

A$^1$–A$^4$ are independently CR$^5$, or up to two of A$^1$–A$^4$ can be N;

R$^5$ is independently at each occurrence —H, C$_1$–C$_{10}$ alkyl, C$_1$–C$_4$ haloalkyl, C$_1$–C$_4$ haloalkoxy, C$_2$–C$_{10}$ alkenyl, C$_2$–C$_{10}$ alkynyl, C$_3$–C$_6$ cycloalkyl, C$_4$–C$_{12}$ cycloalkylalkyl, —NO$_2$, halogen, —CN, —NR$^6$R$^7$, —NR$^6$COR$^7$, —NR$^6$CO$_2$R$^8$, —COR$^6$ —OR$^7$, —CONR$^6$R$^7$, —CO(NOR$^9$)R$^{11}$, —CO$_2$R$^8$, or —S(O)$_n$R$^{11}$, where C$_1$–C$_{10}$ alkyl, C$_2$–C$_{10}$ alkenyl, C$_2$–C$_{10}$ alkynyl, C$_3$–C$_6$ cycloalkyl and C$_4$–C$_{12}$ cycloalkylalkyl are optionally substituted with 1 to 3 substituents independently selected at each occurrence from C$_1$–C$_4$ alkyl, C$_2$–C$_4$ alkenyl, C$_2$–C$_4$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, —NR$^6$COR$^7$, NR$^6$CO$_2$R$^8$, —COR$^6$—OR$^7$, —CONR$^6$R$^7$, —CO$_2$R$^8$, —CO(NOR$^9$)R$^7$, or —S(O)$_n$R$^{11}$ and wherein two adjacent R$^5$ groups can form a 5–7 membered ring saturated on unsaturated optionally containing 1–2 O or SO$_n$ or 1–3 N heteroatoms optionally substituted with C$_1$–C$_4$ alkyl, C$_2$–C$_6$ alkenyl, C$_2$–C$_6$ alkynyl, C$_3$–C$_6$ cycloalkyl, C$_4$–C$_8$ cycloalkylalkyl, C$_1$–C$_4$ haloalkyl, —NO$_2$, halogen, —CN, —NR$^6$R$^7$, —NR$^6$COR$^7$, —NR$^6$CO$_2$R$^8$, —COR$^6$ —OR$^7$, —CONR$^6$R$^7$, —CO$_2$R$^8$, —CO(NOR$^9$)R$^7$, or —S(O)$_n$R$^{11}$ and not containing any S—S, O—O, S—O or N—S bonds in the ring;

R$^6$ and R$^7$ are independently at each occurrence H, C$_1$–C$_6$ alkyl, C$_1$–C$_4$ haloalkyl, C$_2$–C$_8$ alkoxyalkyl, C$_3$–C$_6$ cycloalkyl, C$_4$–C$_{12}$ cycloalkylalkyl, C$_5$–C$_{12}$ bis(alkoxy)alkyl, aryl, aryl(C$_1$–C$_4$ alkyl)-, heteroaryl or heteroaryl (C$_1$–C$_4$ alkyl)

or

NR$^6$R$^7$ is piperidine, pyrrolidine, piperazine, N-methylpiperazine, morpholine or thiomorpholine;

R$^8$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl), heteroaryl or heteroaryl(C$_1$–C$_4$ alkyl);

R$^9$ and R$^{10}$ are independently at each occurrence selected from H, C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_2$–C$_6$ alkoxyalkyl, C$_4$–C$_7$ cycloalkylalkyl;

R$^{11}$ is independently at each occurrence C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl), heteroaryl, heteroaryl(C$_1$–C$_4$ alkyl), or —NR$^6$R$^7$;

R$^{12}$ is independently at each occurrence C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_4$–C$_7$ cycloalkylalkyl;

R$^{13}$ and R$^{14}$, are independently at each occurrence H, C$_1$–C$_4$ alkyl, C$_1$–C$_4$ haloalkyl, C$_3$–C$_6$ cycloalkyl, C$_4$–C$_{12}$ cycloalkylalkyl, aryl, aryl(C$_1$–C$_4$ alkyl), heteroaryl or heteroaryl(C$_1$–C$_4$ alkyl)-, —COR$^{12}$, —CO$_2$R$^8$, —CONR$^9$, S(O)$_n$R$^{12}$;

aryl is phenyl or naphthyl, each optionally substituted with 1 to 3 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{10}$, —SH, —S(O)$_n$R$^{12}$, —COR$^{12}$, —CO$_2$R$^8$, —OC(O)R$^{12}$, —NR$^9$COR$^9$, —N(COR$^{12}$)$_2$, —NR$^9$CONR$^9$R$^{10}$, —NR$^9$CO$_2$R$^8$, —NR$^9$R$^{10}$, and —CONR$^9$R$^{10}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl pyrazolyl, triazolyl, tetrazolyl, or indazolyl, each optionally substituted with 1 to 3 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{10}$, —SH, —S(O)$_n$R$^{12}$, —COR$^{12}$, —CO$_2$R$^8$, —OC(O)R$^{12}$, —NR$^9$COR$^9$, —N(COR$^{12}$)$_2$, —NR$^9$CONR$^9$R$^{10}$, —NR$^9$CO$_2$R$^8$, —NR$^9$R$^{10}$, and —CONR$^9$R$^{10}$;

heterocyclyl is saturated or partially saturated heteroaryl, optionally substituted with 1 to 3 substituents independently selected at each occurrence from C$_1$–C$_6$ alkyl, C$_3$–C$_6$ cycloalkyl, C$_4$–C$_7$ cycloalkylalkyl, C$_2$–C$_6$ alkenyl, C$_2$–C$_6$ alkynyl, halogen, C$_1$–C$_4$ haloalkyl, cyano, —OR$^{10}$, SH, —S(O)$_n$R$^{12}$, —COR$^{12}$, —CO$_2$R$^{12}$, —OC(O)R$^{12}$, —NR$^9$COR$^9$, —N(COR$^{12}$)$_2$, —NR$^9$CONR$^9$R$^{10}$, —NR$^9$CO$_2$R$^{12}$, —NR$^9$R$^{10}$, and —CONR$^9$R$^{10}$;

n is independently at each occurrence 0, 1 or 2
provided that:
 (a) when Q is $I_a$, $I_b$ or $I_c$ and X is N, $R^1$ is not H; and
 (b) $R^1$ is other than O-alkynyl or S-alkynyl;
[2] In a preferred embodiment, the present invention provides a novel compound of formula I, wherein:
Q is Ia, Ib, Ic;
X is N or $CR^1$;
Y, Z are independently N or $CR^2$;
U, V are >C=G, $CR^{13}R^{14}$, or $NR^{13}$, O, or S without forming O—O, S—O, or S—S bonds;
G is O;
$R^1$ is independently at each occurrence H, $C_1$–$C_4$ alkyl, $C_3$–$C_6$ cycloalkyl, halogen, —CN, —$NR^9R^{10}$, —$NR^9COR^{10}$, $C_1$–$C_4$ haloalkyl, —$COR^{10}$, —$OR^{10}$ or —$S(O)_nR^{12}$;
$R^2$ is independently at each occurrence —H, $C_1$–$C_4$ alkyl, $C_3$–$C_6$ cycloalkyl, halogen, —CN, —$NR^9R^{10}$, —$NR^9COR^{10}$, $C_1$–$C_4$ haloalkyl, —$COR^{10}$, —$OR^{10}$ or —$S(O)_nR^{12}$;
$R^3$ is $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, $C_5$–$C_{10}$ cycloalkenylalkyl, where one carbon in any cycloalkyl may be replaced with O, S or $NR^9$ and each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, $C_5$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halo, $C_1$–$C_4$ haloalkyl, cyano, —$OR^7$, SH, —$S(O)_nR^{11}$, —$COR^6$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$NHR^6SO_2R^8$, —$OC(O)NR^6R^7$, —$N_3$, —$OC(O)OR^7$, —$CO_2H$, aryl, heteroaryl and heterocyclyl;
L is a linker selected from the group consisting of: $CR^4{}_2CR^4{}_2CR^4{}_2$, $CR^4{}_2CR^4=CR^4$, $CR^4{}_2CR^4{}_2$, $CR^4=CR^4$, $CR^4{}_2CR^4{}_2B$, $CR^4=CR^4B$;
$R^4$ is independently selected in each occurrence —H, —$OR^{10}$, —$COR^9$, —$CO_2R^8$, —$CONR^9R^{10}$, —CN, —$NR^9R^{10}$, —$S(O)_nR^{12}{}_1$ halogen, $C_1$–$C_6$ alkyl, $C_1$–$C_4$ haloalkyl, $C_3$–$C_6$ cycloalkyl, $C_2$–$C_6$ alkenyl, $C_2$–$C_6$ alkynyl, aryl or heteroaryl, each optionally substituted with the following functional groups: —$OR^{10}$, —$COR^9$, $CO_2R^8$, —$CONR^9R^1$, —CN, —$NR^9R^1$, —$S(O)_nR^{12}$, halogen, or two $R^4$ taken together form one or two carbonyl(s) or thiocarbonyl(s);
B is O, S $(O)_n$, $NR^{12}$;
$A^1$–$A^4$ are $CR^5$;
$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$ —$OR^7$, —$CONR^6R^7$, —$CO(NOR^9)R^{11}$, —$CO_2R^8$, or —$S(O)_nR^{11}$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$ and wherein two adjacent $R^5$ groups can form a 5–7 membered ring saturated on unsaturated optionally containing 1–2 O or $SO_n$ or 1–3 N heteroatoms optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, —$NR^6CO_2R^8$, —$COR^6$ —$OR^7$, —$CONR^6R^7$, —$CO_2R^8$, —$CO(NOR^9)R^7$, or —$S(O)_nR^{11}$ and not containing any S—S, O—O, S—O or N—S bonds in the ring;
$R^6$ and $R^7$ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;
$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl);
$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;
$R^{11}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl ($C_1$–$C_4$ alkyl), heteroaryl or heteroaryl($C_1$–$C_4$ alkyl), piperidine, pyrrolidine, piperazine, N-methylpiperazine, morpholine or thiomorpholine;
$R^{12}$ is $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;
$R^{13}$ and $R^{14}$ are independently H, $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl)-, —$COR^{12}$, —$CO_2R^8$, —$CONR^9$, —$S(O)_nR^{12}$;
aryl is phenyl or naphthyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;
heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;
heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;
n is independently at each occurrence 0, 1 or 2;
[3] In a more preferred embodiment, the present invention provides a novel compound of formula I, wherein:
Q is IIa, IIb, or IIc;
X is N or $CR^1$;
Y, Z are independently N or $CR^2$;
U, V are >C=G, $CR^{13}R^{14}$, or $NR^{13}$, O, or S without forming O—O, S—O, or S—S bonds;
G is O;

$R^1$ is independently at each occurrence H, $C_1$–$C_4$ alkyl, $C_3$–$C_6$ cycloalkyl, halogen, —CN, —NR$^9$R$^{10}$, —NR$^9$COR$^1$I, $C_1$–$C_4$ haloalkyl, —COR$^{10}$, —OR$^{10}$ or —S(O)$_n$R$^{12}$;

$R^2$ is independently at each occurrence H, $C_1$–$C_4$ alkyl, $C_3$–$C_6$ cycloalkyl, halogen, —CN, —NR$^9$R$^{10}$, —NR$^9$COR$^{10}$, $C_1$–$C_4$ haloalkyl, —COR$^{10}$, —OR$^{10}$ or —S(O)$_n$R$^{12}$;

$R^3$ is $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, $C_5$–$C_{10}$ cycloalkenylalkyl, where one carbon in any cycloalkyl may be replaced with O, S or NR$^9$ and each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, $C_5$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —OR$^7$, SH, —S(O)$_n$R$^{11}$, —COR$^6$, —CO$_2$R$^8$, —OC(O)R$^6$, —NR$^7$COR$^6$, —N(COR$^6$)$_2$, —NR$^7$CONR$^6$R$^7$, —NR$^7$CO$_2$R$^8$, —NR$^6$R$^7$, —CONR$^6$R$^7$, —NHR$^6$SO$_2$R$^8$, —OC(O)NR$^6$R$^7$, —N$_3$, —OC(O)OR$^7$, —CO$_2$H, aryl, heteroaryl and heterocyclyl;

L is a linker selected from the group consisting of: CR$^4$$_2$CR$^4$$_2$CR$^4$$_2$, CR$^4$$_2$CR$^4$=CR$^4$, CR$^4$$_2$CR$^4$$_2$, CR$^4$=CR$^4$, CR$^4$$_2$CR$^4$$_2$B, CR$^4$=CR$^4$B;

$R^4$ is independently selected in each occurrence —H, —OR$^{10}$, —COR$^9$, —CO$_2$R$^8$, —CONR$^9$R$^{10}$, —CN, —NR$^9$R$^{10}$, —S(O)$_n$R$^{12}$, halogen, $C_1$–$C_6$ alkyl, $C_1$–$C_4$ haloalkyl, $C_3$–$C_6$ cycloalkyl, $C_2$–$C_6$ alkenyl, $C_2$–$C_6$ alkynyl, aryl or heteroaryl, each optionally substituted with the following functional groups: —OR$^{10}$, —COR$^9$, CO$_2$R$^8$, —CONR$^9$R$^{10}$, —CN, —NR$^9$R$^{10}$, —S(O)$_n$R$^{12}$, halogen, or two R$^4$ taken together form one or two carbonyl(s) or thiocarbonyl(s);

B is O, S(O)$_n$, NR$^{12}$;

$A^1$–$A^4$ are CR$^5$;

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —NO$_2$, halogen, —CN, —NR$^6$R$^7$, —NR$^6$COR$^7$, —NR$^6$CO$_2$R$^8$, —COR$^6$ —OR$^7$, —CONR$^6$R$^7$, —CO(NOR$^9$)R$^{11}$, —CO$_2$R$^8$, or —S(O)$_n$R$^{11}$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —NO$_2$, halogen, —CN, —NR$^6$R$^7$, —NR$^6$COR$^7$, —NR$^6$CO$_2$R$^8$, —COR$^6$—OR$^7$, —CONR$^6$R$^7$, —CO$_2$R$^8$, —CO(NOR$^9$)R$^7$, or —S(O)$_n$R$^{11}$ and wherein two adjacent R$^5$ groups can form a 5–7 membered ring saturated on unsaturated optionally containing 1–2 O or SO$_n$ or 1–3 N heteroatoms optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —NO$_2$, halogen, —CN, —NR$^6$R$^7$, NR$^6$COR$^7$, NR$^6$CO$_2$R$^8$, —COR$^6$, —OR$^7$, —CONR$^6$R$^7$, —CO$_2$R$^8$, —CO(NOR$^9$)R$^7$, or —S(O)$_n$R$^{11}$ and not containing any S—S, O—O, S—O or N—S bonds in the ring;

$R^6$ and $R^7$ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or NR$^6$R$^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^{11}$ is $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl ($C_1$–$C_4$ alkyl)-, heteroaryl or heteroaryl($C_1$–$C_4$ alkyl), piperidine, pyrrolidine, piperazine, N-methylpiperazine, morpholine or thiomorpholine;

$R^{12}$ is $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^{13}$ and $R^{14}$ are independently H, $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-, —COR$^{12}$, —CO$_2$R$^8$, —CONR$^9$, —S(O)$_n$R$^{12}$;

aryl is phenyl or naphthyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{10}$, SH, —S(O)$_n$R$^{12}$, —COR$^{12}$, —CO$_2$R$^8$, —OC(O)R$^{12}$, —NR$^9$COR$^9$, —N(COR$^{12}$)$_2$, —NR$^9$CONR$^9$R$^{10}$, —NR$^9$CO$_2$R$^8$, —NR$^9$R$^{10}$, and —CONR$^9$R$^{10}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{10}$, SH, —S(O)$_n$R$^{12}$, —COR$^{12}$, —CO$_2$R$^8$, —OC(O)R$^{12}$, —NR$^9$COR$^9$, —N(COR$^{12}$)$_2$, —NR$^9$CONR$^9$R$^{10}$, —NR$^9$CO$_2$R$^8$, —NR$^9$R$^{10}$, and —CONR$^9$R$^1$O;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —OR$^{10}$, SH, —S(O)$_n$R$^{12}$, —COR$^{12}$, —CO$_2$R$^8$, —OC(O) R$^{12}$, —NR$^9$COR$^9$, —N(COR$^{12}$)$_2$, —NR$^9$CONR$^9$R$^{10}$, —NR$^9$CO$_2$R$^8$, —NR$^9$R$^{10}$, and —CONR$^9$R$^{10}$;

n is independently at each occurrence 0, 1 or 2;

[4] In an even more preferred embodiment, the present invention provides a novel compound of formula I, wherein:

Q is Ia and X is N.

[5] In a still more preferred embodiment, the present invention provides a novel compound of formula I, wherein:

Y and Z are N or CR$^2$;

$R^1$ is independently at each occurrence —Me, —Et, halogen, —CN, —CF$_3$, —OMe, —SMe, —NHMe, —NMe$_2$, —COMe, —SOMe, —SO$_2$Me;

$R^2$ is —H, —Me, halogen;

$R^3$ is $C_1$–$C_{10}$ alkyl, $C_2$–$C_{10}$ alkenyl, $C_2$–$C_{10}$ alkynyl, $C_3$–$C_8$ cycloalkyl or $C_4$–$C_{10}$ cycloalkylalkyl, $C_2$–$C_{10}$ alkoxyalkyl, cycloalkenyl, cycloalkenylalkyl, each optionally substituted with 1 to 3 substituents independently selected at each occurrence from $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, halogen, $C_1$–$C_4$ haloalkyl, cyano, —OR$^7$, —SH, —S(O)$_n$R$^{11}$, —CR$^6$—CO$_2$R$^8$, —OC(O) R$^{10}$, —NR$^7$COR$^6$, —N(COR$^6$)$_2$, —NR$^7$CONR$^6$R$^7$, —NR$^7$CO$_2$R$^8$, —NR$^6$R$^7$, —CO$_2$H, —CONR$^6$R$^7$;

L is $CH_2CR^4{}_2CR^4{}_2$, $CR^4{}_2CR^4=CR^4$, $CR^4{}_2CR^4{}_2$, $CR^4=CR^4$, $CR^4{}_2CR^4{}_2B$, $CR^4=CR^4B$, where $R^4$ is H, or $C_1$–$C_2$, substituted with the following functional groups: —$CF_3$, —OMe, —COMe, —$CO_2$Me, —CONHMe, —CN, —$NMe_2$, —SMe, —SOMe, —$SO_2$Me, halogen, or two $R^4$ taken together form a carbonyl;

B is O, S, SO, $SO_2$, NH, NMe;

$A^1$–$A^4$ are $CR^5$, $R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$ —$OR^7$, —$CONR^6R^7$, —$CO(NOR^9)R^{11}$, —$CO_2R^8$, or —$S(O)_n R^{11}$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$— $OR^7$, —$CONR^6R^7$, —$CO_2R^8$, —$CO(NOR^9)R^7$, or —$S(O)_n R^{11}$ and wherein two adjacent $R^5$ groups can form a 5–7 membered ring saturated on unsaturated optionally containing 1–2 O or $SO_n$ or 1–3 N heteroatoms optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, $NR^6CO_2R^8$, —$COR^6$ —$OR^7$, —$CONR^6R^7$–$C_{O2}R^8$, —$CO(NOR^9)R^7$, or —$S(O)_n R^{11}$ and not containing any S—S, O—O, S—O or N—S bonds in the ring;

$R^6$, $R^7$, $R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^8$ is independently at each occurrence $C_1$–$C_4$ alkyl, $C_1$–$C_4$ haloalkyl, $C_3$–$C_6$ cycloalkyl, $C_4$–$C_8$ cycloalkylalkyl;

$R^{11}$ is $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

[6] In a further preferred embodiment, the present invention provides a novel compound of formula I, wherein:

Y and Z are N;

$R^1$ is —Me or halogen;

$R^2$ is —H, —Me, halogen;

$R^3$ is $C_1$–$C_{10}$ alkyl, $C_2$–$C_{10}$ alkenyl, $C_2$–$C_{10}$ alkynyl, $C_3$–$C_8$ cycloalkyl or $C_4$–$C_{10}$ cycloalkylalkyl, $C_2$–$C_{10}$ alkoxyalkyl, cycloalkenyl, cycloalkenylalkyl, each optionally substituted with 1 to 3 substituents independently selected at each occurrence from $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, halogen, $C_1$–$C_4$ haloalkyl, cyano, —$OR^7$, —SH, —$S(O)_n R^{11}$, —$COR^6$, —$CO_2R^8$, —$OC(O)R^{10}$, —$NR^7COR^6$, —$N(COR^6)_2$, —$NR^7CONR^6R^7$, —$NR^7CO_2R^8$, —$NR^6R^7$, —$NHR^6\ SO_2R^8$, —$CO_2H$, —$OC(O)NR^6R^7$, —$N_3$, —$OC(O)OR^7$, —$CONR^6R^7$;

L is a linker selected from the group consisting of: $CH_2CH_2CH_2$, $CH_2CH_2$, CH=CH, $CH_2CH_2O$;

$A^1$, $A^2$, $A^3$ and $A^4$ are carbon substituted independently at each occurrence with $R^5$;

$R^5$ is independently at each ocurrence H, $C_1$–$C_6$ alkyl, $C_1$–$C_4$ haloalkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ alkoxy, —$NO_2$, halogen, —CN, $C_1$–$C_4$ haloalkyl, —$NR^6R^7$, —$NR^6COR^7$, —$NR^6CO_2R^8$, —$COR^{11}$—$OR^7$, —$CONR^6R^7$, —$CO(NOR^9)R^{11}$, —$CO_2R^8$, or —$S(O)_n R^{11}$;

$R^6$, $R^7$, and $R^9$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^8$, $R^{11}$ are independently at each occurrence $C_1$–$C_4$ alkyl, $C_1$–$C_4$ haloalkyl, $C_3$–$C_6$ cycloalkyl, $C_4$–$C_8$ cycloalkylalkyl;

[7] In another preferred embodiment, the present invention provides a novel compound of formula I, wherein the compound is selected from the group:

(R,S)-4-(5,7-dibromo-2,3-dihydro-1H-indol-1-yl)-1-[1-methoxyethyl)propyl]-6-methyl-1H-1,2,3-triazolo[4,5-c] pyrimidine;

(R,S)-4-(5,7-dichloro-2,3-dihydro-4-indol-1-yl)-1-[1-methoxyethyl)propyl]-6-methyl-1H-1,2,3-triazolo[4,5-c] pyrimidine;

4-(7-chloro-5-methylsulfonyl-2,3-dihydro-4-indol-1-yl)-1-[1-methoxyethyl)propyl]-6-methyl-1H-1,2,3-triazolo[4,5-c] pyrimidine;

4-(7-chloro-5-methoxy-2,3-dihydro-4-indol-1-yl)-1-[1-methoxyethyl)propyl]-6-methyl-1H-1,2,3-triazolo[4,5-c] pyrimidine;

4-(7-chloro-5-methyl-2,3-dihydro-4-indol-1-yl)-1-[1-methoxyethyl)propyl]-6-methyl-1H-1,2,3-triazolo[4,5-c] pyrimidine;

4-(7-chloro-5-ethyl-2,3-dihydro-4-indol-1-yl)-1-[1-methoxyethyl)propyl]-6-methyl-1H-1,2,3-triazolo[4,5-c] pyrimidine;

4-(7-chloro-5-cyano-2,3-dihydro-4-indol-1-yl)-1-[1-methoxyethyl)propyl]-6-methyl-1H-1,2,3-triazolo[4,5-c] pyrimidine;

4-(5-acetyl-7-chloro-2,3-dihydro-4-indol-1-yl)-1-[1-methoxyethyl)propyl]-6-methyl-1H-1,2,3-triazolo[4,5-c] pyrimidine;

4-(7-chloro-5-thiomethyl-2,3-dihydro-4-indol-1-yl)-1-[1-methoxyethyl)propyl)-6-methyl-1H-1,2,3-triazolo[4,5-c] pyrimidine; and 4-(7-chloro-5-methylsulfonyl-2,3-dihydro-4-indol-1-yl)-1-[1-methoxyethyl)propyl]-6-methyl-1H-1,2,3-triazolo[4, 5-c] pyrimidine.

[8] In another more preferred embodiment, the present invention provides a novel compound of formula I, wherein: Q is Ia and X is $CR^1$.

[9] In another more preferred embodiment, the present invention provides a novel compound of formula I, wherein:

Y and Z are N or $CR^2$;

$R^1$ is independently at each occurrence —Me, —Et, halogen, —CN, —$CF_3$, —OMe, —SMe, —NHMe, —$NMe_2$, —COMe, —SOMe. —$SO_2$Me;

$R^2$ is —H, —Me, halogen;

$R^3$ is $C_1$–$C_{10}$ alkyl, $C_2$–$C_{10}$ alkenyl, $C_2$–$C_{10}$ alkynyl, $C_3$–$C_8$ cycloalkyl or $C_4$–$C_{10}$ cycloalkylalkyl, $C_2$–$C_{10}$ alkoxyalkyl, cycloalkenyl, cycloalkenylalkyl, each optionally substituted with 1 to 3 substituents independently selected at each occurrence from $C_1$–$C_6$ alkyl, $C_2$–$C_6$ alkenyl, $C_2$–$C_6$ alkynyl, $C_3$–$C_6$ cycloalkyl, $C_4$–$C_8$ cycloalkylalkyl, halogen, $C_1$–$C_4$ haloalkyl, cyano, —$OR^7$, —SH, —$S(O)_n R^{11}$, —$COR^6$, —$CO_2R^8$, —$OC(O)R^{10}$, —$NR^7COR^6$, —$CO_2H$, —$N(COR^6)_2$, —$NR^7CONR^6R^7$, —$NR^7CO_2R^8$, —$NR^6R^7$, —$NHR^6SO_2R^8$, —$OC(O)NR^6R^7$, —$N_3$, —$OC(O)OR^7$ and —$CONR^6R^7$;

L is a linker selected from the group consisting of: $CH_2CR^4{}_2CR^4{}_2$, $CR^4{}_2CR^4=CR^4$, $CR^4{}_2CR^4{}_2$, $CR^4=CR^4$, $CR^4{}_2CR^4{}_2B$, $CR^4=CR^4B$, where $R^4$ is H, or $C_1$–$C_2$, substituted with the following functional groups: —$CF_3$, —OMe, —COMe, —$CO_2$Me, —CONHMe, —CN, —$NMe_2$, —SMe, —SOMe, —$SO_2$Me, halogen, or two $R^4$ taken together form a carbonyl;

$R^4$ is independently selected in each occurrence —H, —$OR^{10}$, —$COR^9$, —$CO_2R^8$, —$CONR^9R^{10}$, —CN, —NR$^9$R$^{10}$, —S(O)$_n$R$^{12}$ halogen, C$_1$–C$_6$ alkyl, C$_1$–C$_4$ haloalkyl, C$_3$–C$_6$ cycloalkyl, C$_2$–C$_6$ alkenyl, C$_2$–C$_6$ alkynyl, aryl or heteroaryl, each optionally substituted with the following functional groups: —OR$^{10}$, —COR$^9$, CO$_2$R$^8$, —CONR$^9$R$^{10}$, —CN, —NR$^9$R$^{10}$, —S(O)$_n$R$^{12}$, halogen, or two R$^4$ taken together form one or two carbonyl(s) or thiocarbonyl(s);

B is O, S, SO, SO$_2$, NH, NMe;

A$^1$–A$^4$ are CR$^5$,

R$^5$ is independently at each occurrence H, C$_1$–C$_6$ alkyl, C$_1$–C$_4$ haloalkyl, C$_2$–C$_6$ alkenyl, C$_2$–C$_6$ alkynyl, C$_3$–C$_6$ cycloalkyl, C$_4$–C$_8$ cycloalkylalkyl, —NO$_2$, halogen, —CN, C$_1$–C$_4$ haloalkyl, —NR$^6$R$^7$, NR$^6$COR$^7$, NR$^6$CO$_2$R$^8$, —COR$^{11}$—OR$^7$, —CONR$^6$R$^7$, —CO(NOR$^9$)R$^{11}$, CO$_2$R$^8$, or —S(O)$_n$R$^{11}$, where C$_1$–C$_6$ alkyl, C$_2$–C$_6$ alkenyl, C$_2$–C$_6$ alkynyl, C$_3$–C$_6$ cycloalkyl and C$_4$–C$_8$ cycloalkylalkyl are optionally substituted with 1 to 3 substituents independently selected at each occurrence from C$_1$–C$_4$ alkyl, C$_2$–C$_4$ alkenyl, C$_2$–C$_4$ alkynyl, C$_3$–C$_6$ cycloalkyl, C$_4$–C$_8$ cycloalkylalkyl, C$_1$–C$_4$ haloalkyl, —NO$_2$, halo, —CN, —NR$^6$R$^7$, —NR$^6$COR$^7$, NR$^6$CO$_2$R$^8$, —COR$^6$—OR$^7$, —CONR$^6$R$^7$, CO$_2$R$^8$, —CO(NOR$^9$)R$^7$ and —S(O)$_n$R$^{11}$;

R$^6$, R$^7$, R$^9$ and R$^{10}$ are independently at each occurrence selected from H, C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_4$–C$_7$ cycloalkylalkyl;

R$^8$ is independently at each occurrence C$_1$–C$_4$ alkyl, C$_1$–C$_4$ haloalkyl, C$_3$–C$_6$ cycloalkyl, C$_4$–C$_8$ cycloalkylalkyl;

R$^{11}$ is C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_4$–C$_7$ cycloalkylalkyl.

[10] In another still more preferred embodiment, the present invention provides a novel compound of formula I, wherein:

Y and Z are N;

R$^1$ is —Me or halogen;

R$^2$ is —H, —Me, halogen;

R$^3$ is C$_1$–C$_{10}$ alkyl, C$_2$–C$_{10}$ alkenyl, C$_2$–C$_{10}$ alkynyl, C$_3$–C$_8$ cycloalkyl or C$_4$–C$_1$O cycloalkylalkyl, C$_2$–C$_{10}$ alkoxyalkyl, cycloalkenyl, cycloalkenylalkyl, each optionally substituted with 1 to 3 substituents independently selected at each occurrence from C$_1$–C$_6$ alkyl, C$_2$–C$_6$ alkenyl, C$_2$–C$_6$ alkynyl, C$_3$–C$_6$ cycloalkyl, C$_4$–C$_8$ cycloalkylalkyl, halogen, C$_1$–C$_4$ haloalkyl, cyano, —OR$^7$, —SH, —S(O)$_n$R$^1$l, —COR$^6$, —CO$_2$R$^8$, —OC(O)R$^{10}$, —NR$^7$COR$^6$, —N(COR$^6$)$_2$, —NR$^7$CONR$^6$R$^7$, —NR$^7$CO$_2$R$^8$, —NR$^6$R$^7$, —CO$_2$H, —NHR$^6$SO$_2$R$^8$, —OC(O)NR$^6$R$^7$, —N$_3$, —OC(O)OR$^7$, —CONR$^6$R$^7$;

L is a linker selected from the group consisting of: CH$_2$CH$_2$CH$_2$, CH$_2$CH$_2$, CH=CH, CH$_2$CH$_2$O;

A$^1$, A$^2$, A$^3$ and A$^4$ are carbon substituted independently at each occurrence with R$^5$;

R$^5$ is independently at each ocurrence H, C$_1$–C$_6$ alkyl, C$_1$–C$_4$ haloalkyl, C$_2$–C$_6$ alkenyl, C$_2$–C$_6$ alkynyl, C$_3$–C$_6$ cycloalkyl, C$_4$–C$_8$ cycloalkylalkyl, C$_1$–C$_4$ alkoxy, —NO$_2$, halogen, —CN, C$_1$–C$_4$ haloalkyl, —NR$^6$R$^7$, —NR$^6$COR$^7$, —NR$^6$CO$_2$R$^8$, —COR$^{11}$—OR$^7$, —CONR$^6$R$^7$, —CO(NOR$^9$)R$^1$l, —CO$_2$R$^8$, or —S(O)$_n$R$^{11}$;

R$^6$, R$^7$, and R$^9$ are independently at each occurrence selected from H. C$_1$–C$_4$ alkyl, C$_1$–C$_4$ haloalkyl, C$_3$–C$_6$ alkenyl, C$_3$–C$_6$ alkynyl, C$_3$–C$_6$ cycloalkyl, C$_4$–C$_7$ cycloalkylalkyl;

R$^8$,R$^1$l are independently at each occurrence C$_1$–C$_4$ alkyl, C$_1$–C$_4$ haloalkyl, C$_3$–C$_6$ cycloalkyl, C$_4$–C$_8$ cycloalkylalkyl;

[11] In another preferred embodiment, the present invention provides a novel compound of formula I, wherein the compound is selected from the group:

(S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyridine;

(R,S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyridine;

(R,S)-4-(5,7-dibromo-2,3-dihydro-1H-indol-1-yl)-1-[1-(methoxymethyl)propyl]-6-methyl-1H-1,2,3-triazolo[4,5-c]pyridine;

4-(5,7-dimethoxy-2,3-dihydro-1H-indol-1-yl)-1-1-ethylpropyl]-6-methyl-1H-1,2,3-triazolo[4,5-c]pyridine;

(R,S)-4-(5-bromo-7-methoxy-2,3-dihydro-1H-indol-1-yl)-1-[1-(methoxymethyl)propyl]-6-methyl-1H-1,2,3-triazolo[4,5-c]pyridine;

(R,S)-4-(5-bromo-7-methoxy-2,3-dihydro-1H-indol-1-yl)-1-[1-(methoxymethyl)-3-methoxypropyl]-6-methyl-1H-1,2,3-triazolo[4,5-c]pyridine;

(R,S)-4-(5-bromo-7-methyl-2,3-dihydro-1H-indolyl)-1-[1-(methoxymethyl)propyl-6-methyl-1H-1,2,3-triazolo[4,5-c]pyridine;

(R,S)-4-(5-bromo-7-chloro-2,3-dihydro-1H-indol-1-yl)-1-(1-methoxymethyl)propyl]-6-methyl-1H-1,2,3-triazolo[4,5-c]pyridine;

(R,S)-4-(5-bromo-7-chloro-2,3-dihydro-1H-indol-1-yl)-1-[1-(methoxymethyl)-3-methoxypropyl]6-methyl-1H-1,2,3-triazolo[4,5-c]pyridine;

(R,S)-4-(7-chloro-5-methoxy-2,3-dihydro-1H-indol-1-yl)-1-[1-(methoxymethyl)-3-methoxypropyl]-6-methyl-1H-1,2,3-triazolo[4,5-c]pyridine;

(S)-4-(7-chloro-5-methoxy-2,3-dihydro-1H-indol-1-yl)-1-[1-(methoxymethyl)propyl]-6-methyl-1H-1,2,3-triazolo[4,5-c]pyridine;

(R,S)-4-(7-chloro-5-methyl-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-ethyl-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-cyano-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-thiomethyl-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-methoxy-2,3-dihydro-1H-indol-1-yl)-1-[1-(methoxymethy)propyl]-6-methyl-1H-1,2,3-triazolo[4,5-c]pyridine;

(R,S)-4-(7-chloro-5-methyl-2,3-dihydro-1H-indol-1-yl)-1-[1-(methoxymethyl)propyl]-6-methyl-1H-1,2,3-triazolo[4,5-c]pyridine;

(R,S)-4-(7-chloro-5-ethyl-2,3-dihydro-1H-indol-1-yl)-1-[1-(methoxymethy)propyl]-6-methyl-1H-1,2,3-triazolo[4,5-c]pyridine;

(R,S)-4-(7-chloro-5-cyano-2,3-dihydro-1H-indol-1-yl)-1-[1-(methoxymethy)propyl]-6-methyl-1H-1,2,3-triazolo[4,5-c]pyridine;

4-(7-chloro-5-thiomethyl-2,3-dihydro-1H-indol-1-yl)-1-(1-ethylpropyl)-6-methyl-1H-1,2,3-triazolo[4,5-c]pyridine;

4-(7-chloro-5-methylsulfonyl-2,3-dihydro-1H-indol-1-yl)-1-(1-ethylpropyl)-6-methyl-1H-1,2,3-triazolo[4,5-c]pyridine;

4-(7-chloro-5-methoxy-2,3-dihydro-1H-indol-1-yl)-1-(1-ethylpropyl)-6-methyl-1H-1,2,3-triazolo[4,5-c]pyridine;

4-(7-chloro-5-methyl-2,3-dihydro-1H-indol-1-yl)-1-(1-ethylpropyl)-6-methyl-1H-1,2,3-triazolo[4,5-c]pyridine;

4-(7-chloro-5-ethyl-2,3-dihydro-1H-indol-1-yl)-1-(1-ethylpropyl)-6-methyl-1H-1,2,3-triazolo[4,5-c]pyridine;

4-(7-chloro-5-cyano-2,3-dihydro-1H-indol-1-yl)-1-(1-ethylpropyl)-6-methyl-1H-1,2,3-triazolo[4,5-c]pyridine;

4-(5-acetyl-7-chloro-2,3-dihydro-1H-indol-1-yl)-1-(1-ethylpropyl)-6-methyl-1H-1,2,3-triazolo[4,5-c]pyridine;

4-(7-chloro-5-methylsulfonyl-2,3-dihydro-1H-indol-1-yl)-1-(1-ethylpropyl)-6-methyl-1H-1,2,3-triazolo[4,5-c]pyridine;

4-(5,7-dichloro-2,3-dihydro-1H-indol-1-yl)-1-(1-ethylpropyl)-6-methyl-1H-1,2,3-triazolo[4,5-c]pyridine;

(R,S)-4-(5,7-dichloro-2,3-dihydro-1H-indol-1-yl)-1-[1-(methoxymethyl)propyl]-6-methyl-1H-1,2,3-triazolo[4,5-c]pyridine;

(R,S)-4-(5,7-dichloro-2,3-dihydro-1H-indol-1-yl)-1-[1-(methoxymethyl)-3-methoxypropyl]-6-methyl-1H-1,2,3-triazolo[4,5-c]pyridine;

4-(5,7-dichloro-2,3-dihydro-1H-indol-1-yl)-1-[1-(methoxyethyl)-3-methoxypropyl]-6-methyl-1H-1,2,3-triazolo[4,5-c]pyridine;

(R,S)-4-(5,7-dichloro-2,3-dihydro-1H-indol-1-yl)-1-[1-(cyanomethyl)propyl]-6-methyl-1H-1,2,3-triazolo[4,5-c]pyridine;

N-(7-chloro-5-methoxy-1H-indol-1-yl)-1-(1-ethylpropyl)-6-methyl-1H-1,2,3-triazolo[4,5-c]pyridine;

N-(7-chloro-5-methyl-1H-indol-1-yl)-1-(-ethylpropyl)-6-methyl-1H-1,2,3-triazolo [4,5-c] pyridine;

N-(7-chloro-5-methyl-1H-indol-1-yl)-1-(1-ethylpropyl)-6-methyl-1H-1,2,3-triazolo[4,5-c]pyridine;

N-(7-chloro-5-cyano-1H-indol-1-yl)-1-(1-ethylpropyl)-6-methyl-1H-1,2,3-triazolo[4,5-c]pyridine;

N-(5-acetyl-7-chloro-1H-indol-1-yl)-1-(1-ethylpropyl)-6-methyl-1H-1,2,3-triazolo[4,5-c]pyridine;

N-(7-chloro-5-thiomethyl-1H-indol-1-yl)-1-(1-(1 ethylpropyl)6-1ethyl-H-1,2,3-triazolo[4ie 5-c]pyridine;

N-(7-chloro-5-methylsulfony-1H-indol-1-yl)-1-(1-ethylpropyl)-6-methyl-1H-1,2,3-triazolo[4,5-c]pyridine;

(R,S)-8-chloro-1,2,3,4-tetrahydro-1-[1-[1-(methoxymethy)propyl]-6-methyl-1H-1,2,3-triazolo[4,5-c]pyridin-4-yl]-6-methylquinoline;

(R,S)-8-bromo-1,2,3,4-tetrahydro-1-[1-[1-(methoxymethy)propyl]-6-methyl-1H-1,2,3-triazolo[4,5-c]pyridin-4-yl]-6-methylquinoline;

(R,S)-8-chloro-6-methoxy-1,2,3,4-tetrahydro-1-[1-[1-(methoxymethy)propyl]-1H-1,2,3-triazolo[4,5-c]pyridin-4-yl]-6-methylquinoline;

(R,S)-8-chloro-6-cyano-1,2,3,4-tetrahydro-1-[1-[1-(methoxymethy)propyl]-1H-1,2,3-triazolo[4,5-c]pyridin-4-yl]-6-methylquinoline;

(R,S)-8-chloro-1,2,3,4-tetrahydro-1-[1-[1-(methoxymethy)propyl]-6-methylsulfonyl-1H-1,2,3-triazolo[4,5-c]pyridin-4-yl]-6-methylquinoline;

8-chloro-1,2,3,4-tetrahydro-1-[1-(1-ethylpropyl)-6-methyl-1H-1,2,3-triazolo[4,5-c]pyridin-4-yl]-6-methylquinoline;

8-bromo-1,2,3,4-tetrahydro-1-[1-(1-ethylpropyl)-6-methyl-1H-1,2,3-triazolo[4,5-c]pyridin-4-yl]-6-methylquinoline;

8-chloro-1,2,3,4-tetrahydro-1-[1-(1-ethylpropyl)-6-methoxy-1H-1,2,3-triazolo[4,5-c]pyridin-4-yl]-6-methylquinoline;

8-chloro-6-cyano-1,2,3,4-tetrahydro-1-[1-(1-ethylpropyl)-6-methyl-1H-1,2,3-triazolo[4,5-c]pyridin-4-yl]-6-methylquinoline;

8-chloro-1,2,3,4-tetrahydro-1-[1-(1-ethylpropyl)-6-methylsulfonyl-1H-1,2,3-triazolo[4,5-c]pyridin-4-yl]-6-methylquinoline;

6-acetyl-8-chloro-1,2,3,4-tetrahydro-1-[1-(1-ethylpropyl)-1H-1,2,3-triazolo[4,5-c]pyridin-4-yl]-6-methylquinoline; and (R,S)-5-bromo-3,4-dihydro-4-[1-[1-(methoxymethyl)propyl]-6-methyl-1H-1,2,3-triazolo[4,5-c]pyridin-4-yl]-7-methyl-2H-1,4-benzoxazine.

The present invention also provides pharmaceutical compositions comprising a pharmaceutically acceptable carrier and a therapeutically effective amount of a compounds of Formula (I) as described above.

The present invention further comprises a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of Formula (I) as described above.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7-to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5-to 7-membered monocyclic or bicyclic or 7-to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5-to 7-membered monocyclic or bicyclic or 7-to 10-membered bicyclic heterocyclic aromatic ring which consists of carbon atoms and from 1 to 4 heterotams independently selected from the group consisting of N, C and S. It is preferred that the total number of S and C atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides,* 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid. The term "amino acid residue" as used herein means that portion of an amino acid (as defined herein) that is present in a peptide.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

The term "therapeutically effective amount" of a compound of this invention means an amount effective to antagonize abnormal level of CRF or treat the symptoms of affective disorder, anxiety or depression in a host.

Synthesis

The bicylic fused pyrimidine and pyridines of this invention can be prepared by one of the general schemes outlined below (Schemes 1–15).

Compounds of the Formula (I) wherein X and Y are

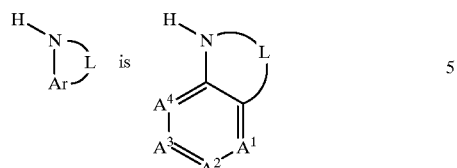

can be prepared as shown in Scheme 1.

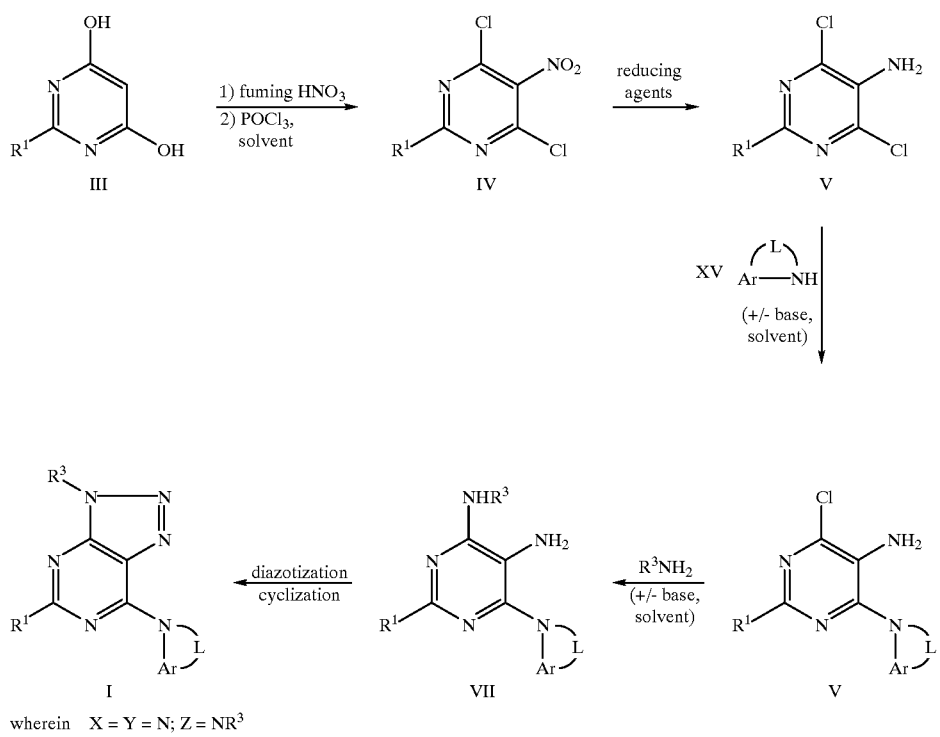

The 4,6-dihydroxypyrimidines (III) can be nitrated using fuming nitric acid and then converted into intermediates (IV) by the action of phosphorous oxychloride with the optional assistance of a catalyst such as dialkylanilines (see: Brown, D. J. et.al. *J. Chem. Soc.,* 1954, 3832). The amino group of pyrimidines of Formula (V) can be prepared from the corresponding nitro compounds (IV) by treatment with reducing agents such as, but not limited to, sodium dithionate, iron or zinc, or catalytic hydrogenation (see: Larock, R. C. *Comprehensive Organic Transformations*, VCH Publishers, New York, 1989, 411). Reaction with compounds of Formula —Ar—L—NH— (XV), can be used to provide compounds of Formula (VI). Conditions which may facilitate this transformation include the optional presence of protic or aprotic acids, or bases such as alkali metal hydrides, trialkylamines, or alkali metal carbonates, or alkali metal bis(trimethylsilyl)amides wherein the metal can be sodium, lithium, or potassium. These reactions may be conducted neat, or in the optional presence of solvents such as but not limited to cyclic ethers such as tetrahydrofuran, dialkylformamides, ethylene glycol, 2-ethoxyethanol, halocarbons, alkanenitriles, or alkyl alcohols at room temperature or at elevated temperature up to the boiling point of the solvent employed. One skilled in the art of organic synthesis will readily understand the optimal combinations of these conversions to prepare a number of compounds of Formula (VI). Treatment of compound of Formula (VI) with primary amines then can provide the intermediates (VII) using reaction conditions similar to those employed for the conversion of (V) to (VI). Cyclization to triazolopyrimidines of Formula (I) can then be readily accomplished by diazotization and cyclization of the diamino compounds of Formula (VII) with an alkali metal nitrite in the presence of acid in water with or without an organic cosolvent such as halocarbons, or cyclic ethers.

Alternatively, compounds of Formula (I) wherein X and Y are N and Z is $NR^3$, of this invention can be prepared as outlined in Scheme 2:

Scheme 2

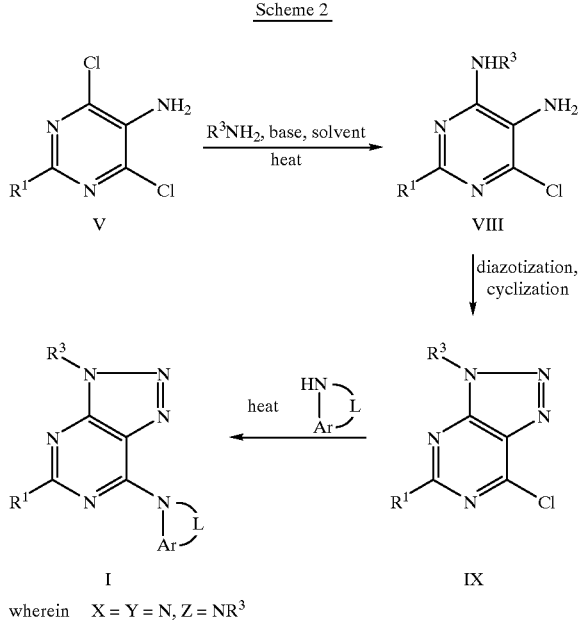

wherein  X = Y = N, Z = NR³

Treatment of compound of Formula (V) with primary amines can provide the diamino substituted pyrimidines (VIII). Conditions which facilitate this transformation are detailed previously for the conversion of (VI) to (VII). Cyclization to triazolopyrimidines of Formula (VIII) can then be readily accomplished by following the conditions already described for the conversion of (VII) to (I) in Scheme 1. The leaving group such as, but not limited to, halogen can then be displaced by addition of —Ar—L—NH— to provide compounds of Formula (I) by utilizing the conditions described for the conversion of (V) to (VI).

Compounds of the Formula (VI) can also prepared by an another approach (Scheme 3) involving addition of —Ar—L—NH— to (IV) to afford compounds of Formula (XI).

Scheme 3

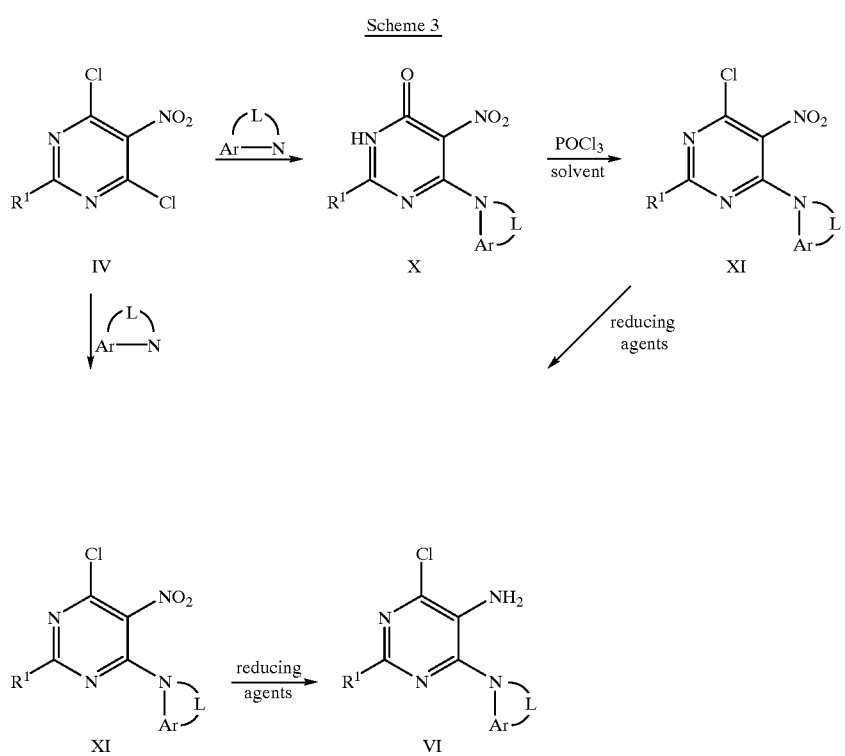

The nitro group in (XI) can be reduced to give compounds of Formula (VI) under conditions similar to those described for the transformation of (IV) to (V) in Scheme 1. Alternatively, as shown in Scheme 3, addition of —Ar—L—NH— to compounds of Formula (IV) can generate in-situ the pyrimidones (X). For example, treatment of dichloropyrimidines of Formula (IV) with one equivalent of —Ar—L—NH— in the presence of solvents such as (but not limited to) dialkylsulfoxides, dialkylformamides, and alkyl alcohols readily generate pyrimidones (X). Compounds of Formula (X) can be converted into (XI) by the action of phosphorous oxychloride with the optional assistance of a catalyst such as dialkylanilines with or without an inert solvent. Compounds of Formula (XI) can be reduced to give (IV) under conditions described in Scheme 1. Compounds of Formula (VI) are elaborated to structures of Formula (I) as previously shown in Scheme 1.

Scheme 4 outlines another route to fused triazolopyrimidine type of compounds of this invention.

Scheme 5

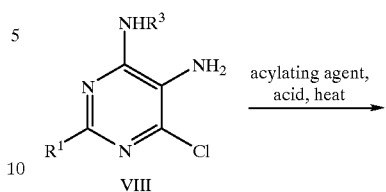

VIII

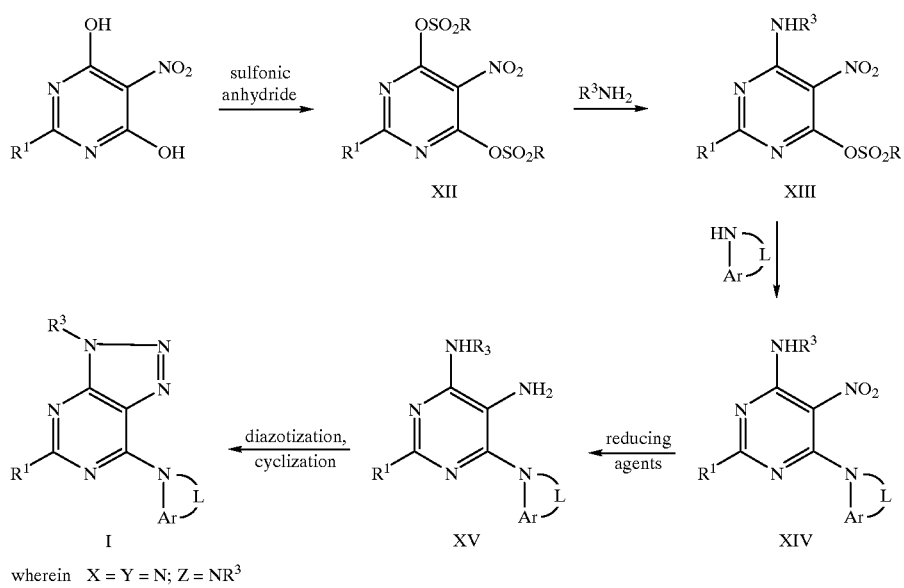

Scheme 4 wherein X = Y = N; Z = NR³

4,6-dihydroxy-5-nitropyrimidines can be treated with aryl sulfonic anhydrides, aryl sulfonyl chlorides, alkyl sulfonic anhydrides or alkyl sulfonyl chlorides in the presence or absence of bases such as alkali metal hydrides, alkaline earth metal hydrides, alkali metal dialkyl amides in inert solvents such as dialkylformamides, dialkylacetamides at temperatures ranging from 0° to 200° C. to give intermediates of Formula (XII). Compounds of Formula (XII) are treated with primary amines to give aminonitropyrimidines (XIII). Treatment of (XIII) with —Ar—L—NH— can provide compounds of Formula (XIV). Compounds of the formula (XIV) can be reduced to amino derivatives (VII) using the reagents described for the conversion of (IV) to (V) in Scheme 1. Intermediate (VII) can be converted to (I) (X and Y are N; Z is NR³) by diazotization and cyclization as delineated in Scheme 1.

Fused imidazolopyrimidines of the Formula (I) wherein X is N, Y is CR², and Z is NR³, can be prepared from compound (VIII) as shown in Scheme 5.

-continued

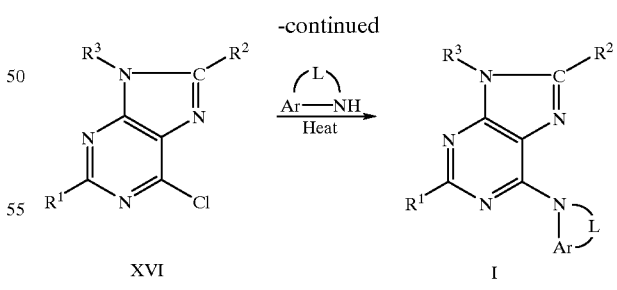

XVI wherein X = N, Y = CR², Z = NR³

Treatment of (VIII) with an acylating agent such as, but not limited to, alkyl anhydrides, haloalkyl anhydrides, alkylamides, haloalkyl amides, trialkylorthoesters R²(OR)₃ (where R is C₁–C₄ alkyl), iminoesters, guanidines, cyanogen bromide, R²COOH, urea or thiourea in the presence or absence of an acid (such as HOAc, HCl, H₂SO₄) in the presence or absence of an organic cosolvent such as alkyl alcohols, cyclic ethers, or aromatic solvents at temperatures ranging from 0° to 200° C. gives compounds of Formula (XVI). Treatment of (XVI) with —Ar—L—NH— can provide imidazolopyrimidine (I, wherein X is N, Y is $CR^2$, Z is $NR^3$).

The method of synthesis of the triazolopyridines of this invention is shown in Scheme 6.

Imidazolopyridines of the present invention can be prepared from compound (XX) as shown in Scheme 6 by following the conditions outlined for the conversion of (VIII) to (XVI) in Scheme 5. Treatment of compound (XXII) with —Ar—L—NH— using the conditions outlined in Scheme 1 can provide compounds of Formula I.

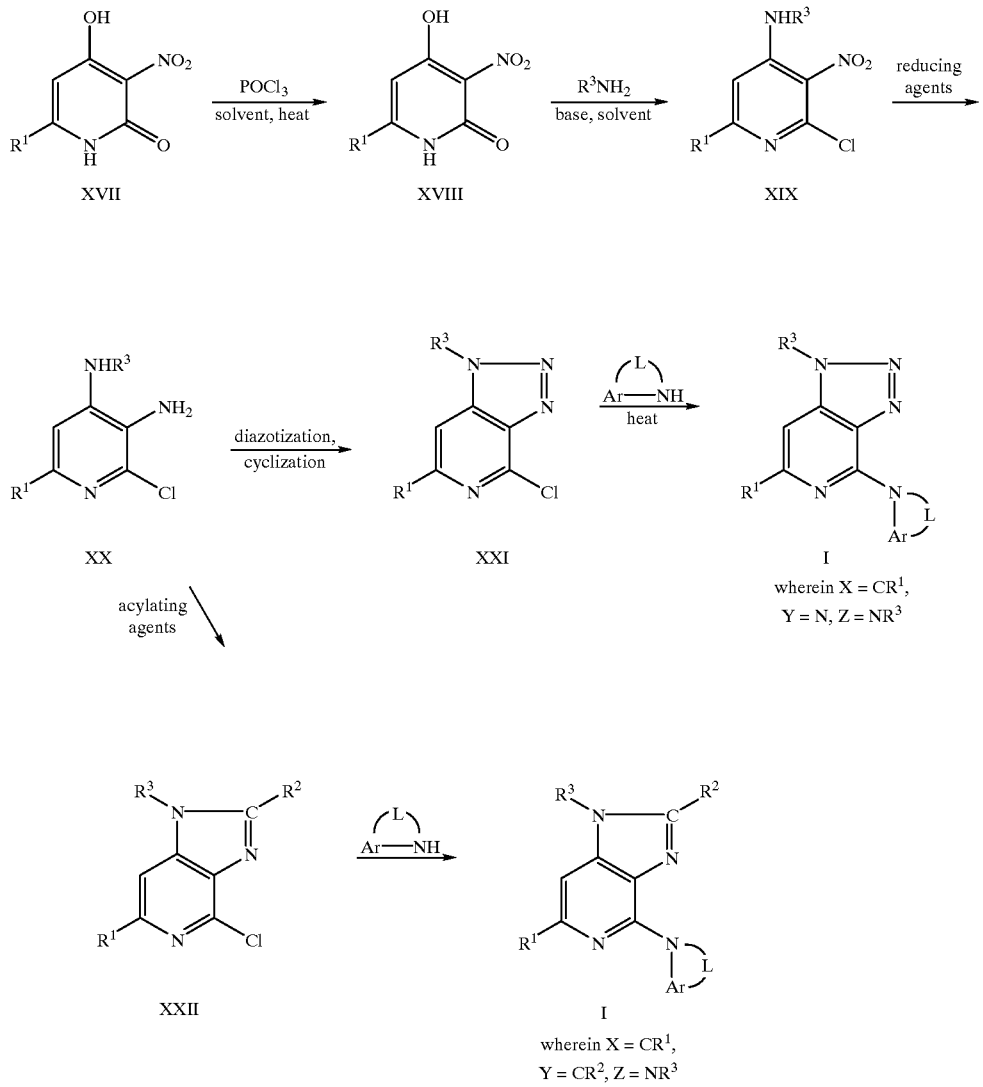

The 4-hydroxy group in (XVII) can be converted into chloro by the action of phosphorous oxychloride with the optional assistance of a catalyst such as dialkylaniline (see: Brown, D. J. et.al. *J. Chem. Soc.*, 1954, 3832) to afford compounds of Formula (XVIII). Addition of primary amines to compound (XVIII) can provide alkylaminonitropyridines (XIX). The nitro group in (XIX) can be reduced using the conditions employed for the transformation of (IV) to (V) in Scheme 1 to give (XX). Diazotization and cyclization of (XX) can provide chlorotriazolopyridine derivatives (XXI) as was described for the conversion of (VI) to (VII) in Scheme 1. The chloro group can then be displaced by addition of —Ar—L—NH— to afford compounds of Formula (I).

Alternatively, the triazolopyridines and imidazolopyridines can be synthesized as shown in Scheme 7. Treatment of compounds of Formula (XVII) with an aliphatic or aromatic amine in the appropriate organic solvent but not limited to, alkyl alcohols such as methanol, ethanol, propanol, butanol, alkyl alkanoates such as ethyl acetate, alkanenitriles such as acetonitrile, dialkyl formamides such as DMF gives the corresponding ammonium salt, which upon treatment with $POCl_3$ at temperatures from 25 to 120° C., give compounds of Formula (XXIII). Treatment of compounds of Formula (XXIII) with appropriate primary amines in an organic solvent such as but not limited to, alkyl alcohols such as methanol, ethanol, propanol, butanol, alkyl alkanoates such as ethyl acetate, alkanenitriles such as acetonitrile, dialkyl formamides such as DMF, dialkylsulfoxides at temperatures from 25 to 120° C. to give (XXIV). This was converted to (XIX) by treatment with POCl₃ at temperatures from 25 to 120 C.

described for the conversion of (VII) to (I) in Scheme I. The chloro group can then be displaced by addition of —Ar—L—NH— in the presence of a base in an inert solvent. Bases include, but are not limited to, alkali metal alkoxides, akali metal hydrides, trialkyl amines, pyridine,

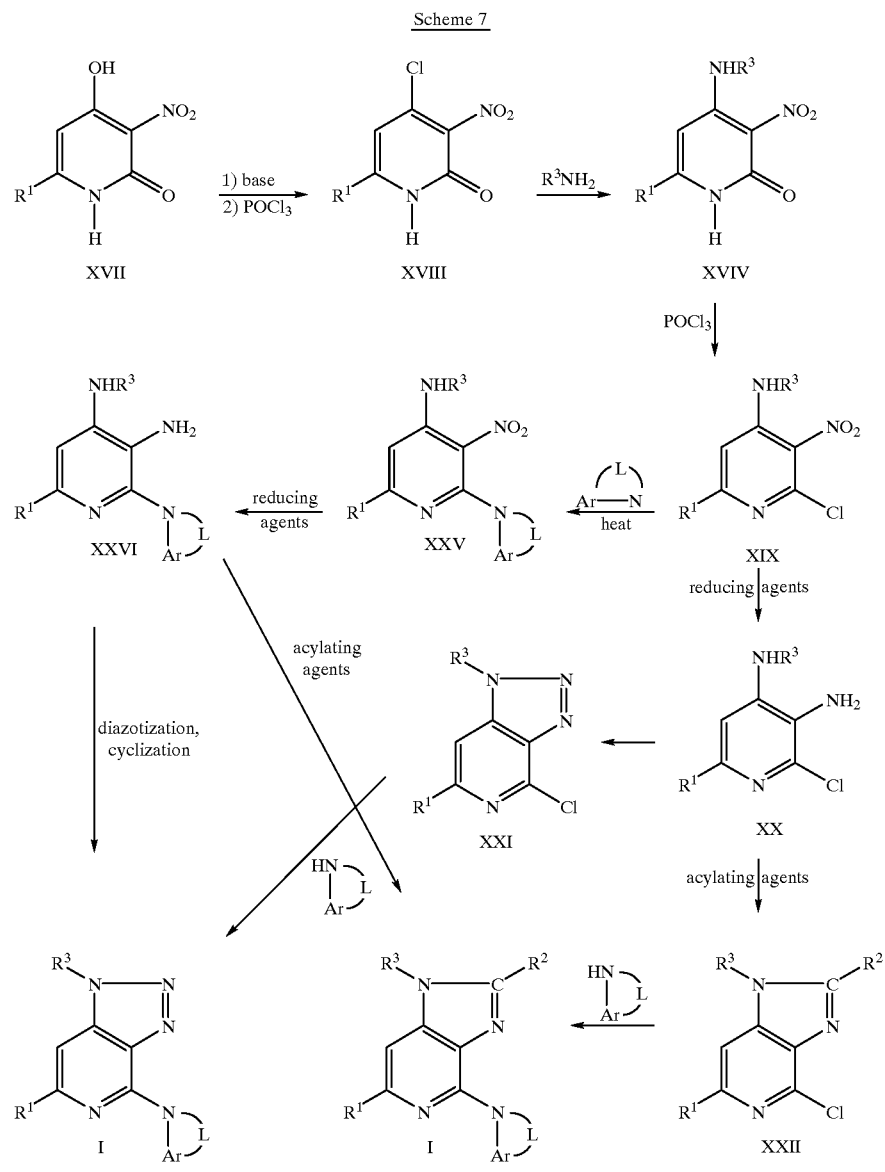

Scheme 7

Compounds of Formula (XIX) could be coupled with —Ar—L—NH— with or without the presence of solvent at temperatures from 25 to 200° C. to give product (XXV), These could be converted to intermediates (XXVI) by reduction of the nitro group under a variety of reducing conditions, such as those used for the conversion of (IV) to (V) in Scheme 1. The final cyclization was carried out as described for the conversion of (VII) to (I) in Scheme 1. Compounds of Formula (XIX) can be converted to intermediates (XX) by reduction of the nitro group under a variety of reducing conditions, such as those used for the conversion of (IV) to (V) in Scheme 1. Diazotization and cyclization of (XX) can provide chlorotriazolopyridine (XXI) as was 4-dimethylaminopyridine, alkali metal dialkyl amides or alkali metal bis(trimethylsilyl)amides. Inert solvents include, but are not limited to, halocarbons, alkanenitriles, dialkylformamides, dialkylacetamides, dialkyl ethers, cyclic ethers such as tetrahydrofuran or dioxane, or alkyl alcohols. The addition can take place in the presence of an acid such as but not limited to HCl, $H_2SO_4$, AcOH, methanesulfonic acid, p-toluenesulfonic acid in inert solvents such as toluene, xylenes at temperatures ranging from 0° to 200° C. to afford product I. The same transformation can be affected under thermal conditions, neat, or in the presence of a high boiling solvent.

Imidazolopyridines can be synthesized from intermediates of Formula (XXII) as described in Scheme 6.

Compounds of general Formula (I, Q is Ib) may be prepared according to the procedures outlined in Scheme 8.

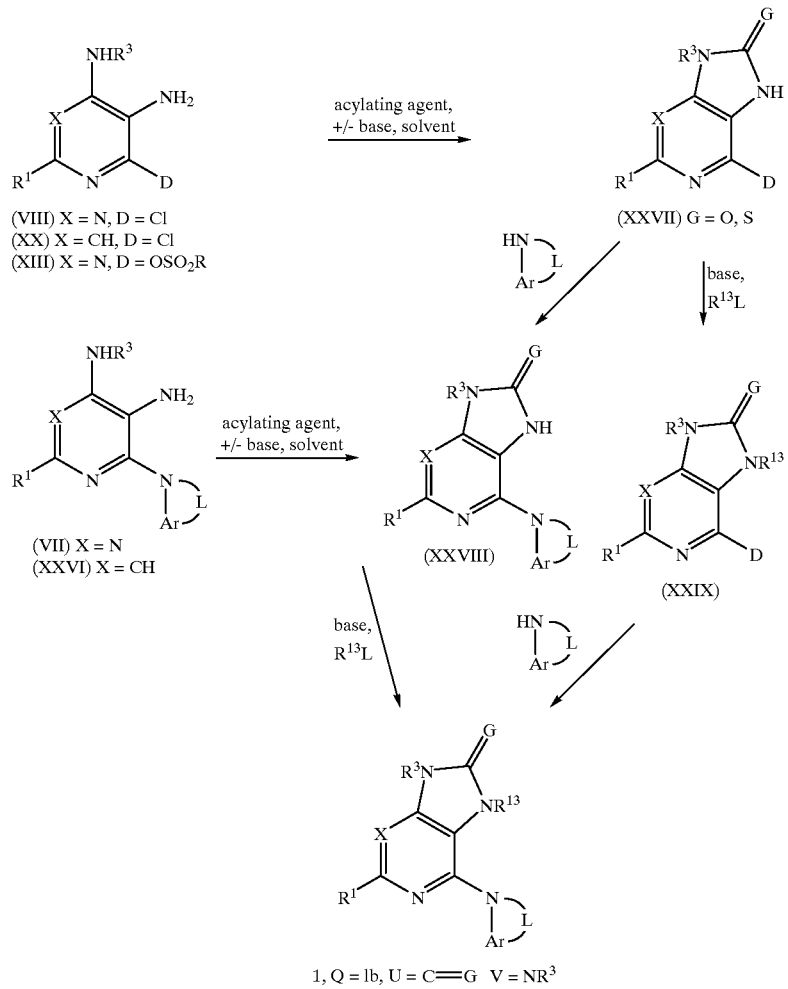

Intermediates of Formula (VIII), (XX) or (XIII) may be converted to compounds of Formula (XXVII) by treatment with an acylating agent in the presence or absence of a base in an inert solvent at reaction temperatures ranging from −78° C. to 200° C. Acylating agents include, but are not limited to, phosgene, thiophosgene, diphosgene, triphosgene, carbonyl diimidazole, thiocarbonyl diimidazole, dialkylcarbonates (such as diethyl carbonate) or $R^aR^bN(C=G)OR^c$ (where G is O, S; $R^a$, $R^b$, and $R^c$ are independently $C_1$–$C_8$ alkyl). Bases include, but are not limited to, alkali metal alkoxides, akali metal hydrides, trialkyl amines, pyridine, 4-dimethylaminopyridine, alkali metal dialkyl amides or alkali metal bis(trimethylsilyl) amides. Inert solvents include, but are not limited to, halocarbons, alkanenitriles, dialkylformamides, dialkylacetamides, dialkyl ethers, cyclic ethers such as tetrahydrofuran or dioxane, or alkyl alcohols. Intermediates of Formula (XXVII) may be converted to compounds of Formula (XXVIII) (Formula (I), where Q is Ib and $R^{13}$ is H) by reaction with —Ar—L—NH—, using the conditions described for the conversion of compound (V) to (VI) in Scheme 1. Compounds of Formula (XXVIII) may be converted to compounds of (Formula (I), where Q is Ib) by treatment with $R^{13}L$ (where L is a leaving group such as halide, alkanesulfonate or arylsulfonate) in the presence or absence of a base in an inert solvent. Bases include, but are not limited to, alkali metal alkoxides, akali metal hydrides, trialkyl amines, pyridine, 4-dimethylaminopyridine, alkali metal dialkyl amides or alkali metal bis(trimethylsilyl) amides. Inert solvents include, but are not limited to, halocarbons, alkanenitriles, dialkylformamides, dialkylacetamides, dialkyl ethers, cyclic ethers such as tetrahydrofuran or dioxane, or alkyl alcohols.

Compounds of Formula (XXIX) may be prepared from compounds of structure (XXVII) by reaction with $R^{13}L$ where L is a leaving group such as halide, alkanesulfonate or arylsulfonate) in the presence or absence of a base in an inert solvent. Bases and inert solvents may be the same as those listed above for the preparation of compounds of Formula (I), (where Q is Ib) from (XXVIII). Intermediates of Formula (XXIX) can be reacted with —Ar—L—NH— to give compounds of Formula (I), (where Q is Ib) using the conditions described for the conversion of compound (V) to (VI) in Scheme 1.

Alternatively intermediates of Formula (VII) and (XXVI) can be converted to compounds of Formula (XXVIII) under similar conditions that may by used for the conversion of (VIII), (XX) or (XIII) to (XXVII).

As shown in Scheme 9, reaction of a 4-alkylamino-3-nitro-pyridone of Formula (XXIV) with a reducing agent, such as $Na_2S_2O_4$ affords the corresponding 4-amino-3-amino-pyridone of Formula (XXX). This transformation can be effected under a variety of reducing conditions, such as catalytic hydrogenation, reducing metal reaction (Fe, Sn, Zn), hydride reaction ($NaBH_4$, $LiAlH_4$) etc., which are known to those skilled in the art. The 4-amino-3-amino-pyridone can be converted to the triazolopyridone of formula (XXXI) by treatment with an alkali metal nitrite, such as $NaNO_2$, under acidic conditions. The resulting triazolopyridone can be converted to the corresponding halo-triazolopyridine of Formula (XXXII)(X is Cl or Br), by treatment with a halogenating agent such as $POCl_3$, $PBr_3$, $POBr_3$. Alternatively X can be an appropriate leaving group resulting from treatment of the triazolopyridone with triflic, tosic or mesyl anhydride in the presence of a base. The triazolopyridine can be coupled with arylamines —Ar—L—NH— under acidic, basic or thermal catalysis (conditions described in Scheme 7) to compounds of Formula I.

Scheme 9

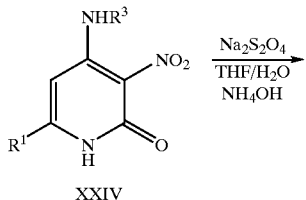

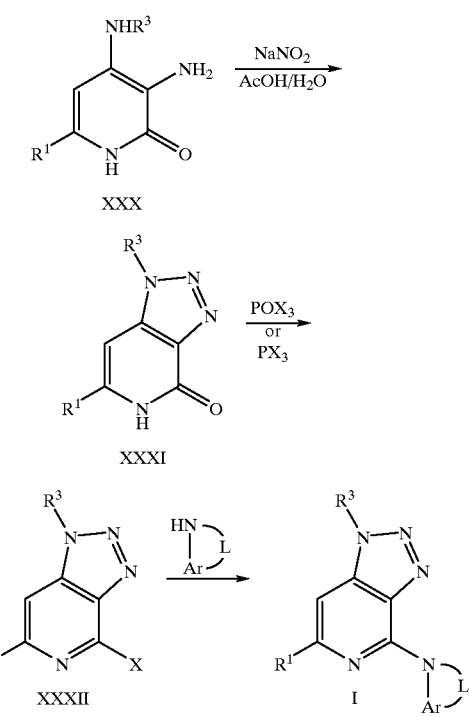

The $R^5$ substituents on the aryl ring can be further modified by reactions described in Scheme 10.

Scheme 10

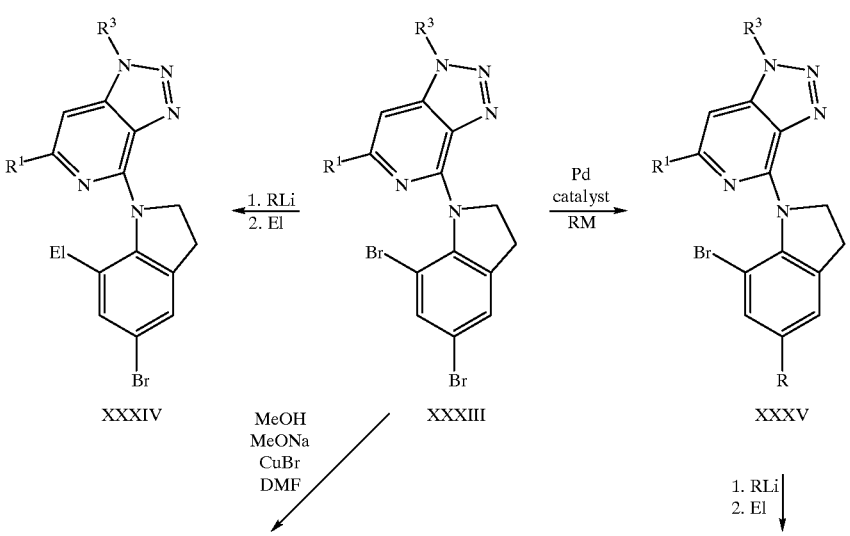

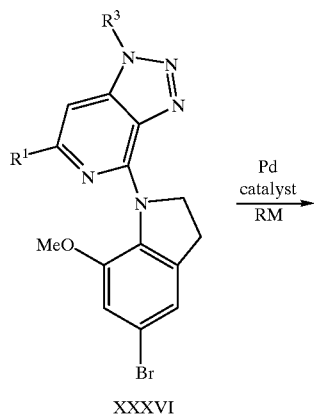
XXXVI

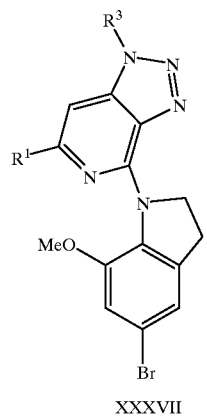
XXXVII

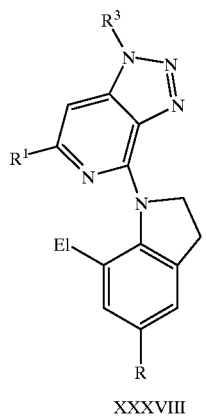
XXXVIII

The dibromo analog (XXXIII) of Formula (I) (where X is CH, Y is N, L is CH₂—CH₂) was treated with an alkyllithium such as n-butyllithium in an aprotic solvent at low temperature to affect Br/Li exchange. The aryllithium intermediate was further reacted with an electrophile to give the 7-substituted analog (XXXIV). Alternatively the 5-bromo substituent of the indoline could selectively react with various vinyltrialkyltin, vinylboronic acid reagents, or thiol salts in the presence of a palladium catalyst to give the 5-substituted analogs of Formula (XXXV). These analogs could be further reacted with an alkyllithium followe by an electrophile to give analogs of Formula (XXXVIII).

Compounds of Formula (XXXIII) could be converted to the 7-methoxy analogs (XXXVI) by treatment with MeONa/MeOH in DMF under copper (I) salt catalysis. The 5-bromo substituent of these analogs could be further elaborated by the employing conditions described for the transformation of (XXXV) to (XXXVIII). In all cases the indoline ring may be dehydrogenated to the corresponding indole analogs by employing known methods described in the chemical literature.

Compounds of Formula I may be synthesized as described in Scheme 11.

Scheme 11

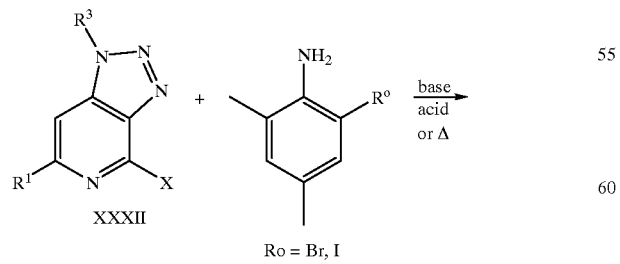
XXXII
Ro = Br, I

-continued

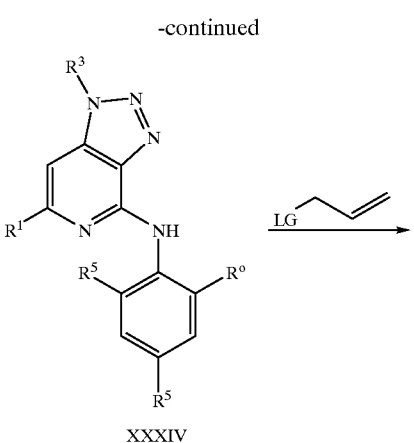
XXXIV

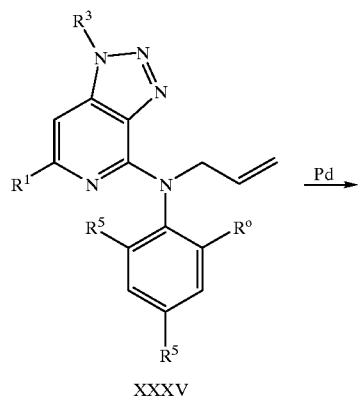
XXXV

-continued

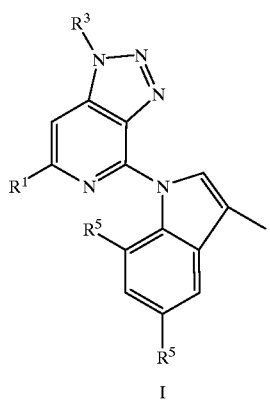

I

Coupling a suitably substituted aniline having an ortho —Br, —I, or —OSO$_2$CF$_3$ group with a triazolopyridine of Formula (XXXII) under base, acid or thermal catalysis gives the coupled product of Formula (XXXIV). The central nitrogen of (XXXIV) was allylated by treatment with a base such as NaH in an aprotic solvent to give (XXXV). This in turn may be subjected to a palladium-catalyzed ring closure (see: Larock, R. C et. al. *Tetrahedron Let.*, 1987, 44, 5291) to give compounds of Formula (I) (L is —CH=CR—).

Alternatively other analogs with the Formula (I) can be obtained by transformations described on Scheme 12.

Reaction of compounds of Formula (XXXIV) with a suitably substituted acetylene using a suitable palladium catalyst (see: Heck, R. F. et. al. *Acc. Chem. Res.*, 1979, 12, 146) may provide the corresponding acetylenic aryls of Formula (XXXVI). Depending on the original substitution on the acetylene, compounds of Formula (XXXVI) can be converted to the 2-alkylindole analogs (Formula I in which L is —CR=CH—), or the indolinones (Formula I in which L is —CO—CH$_2$—).

Scheme 12

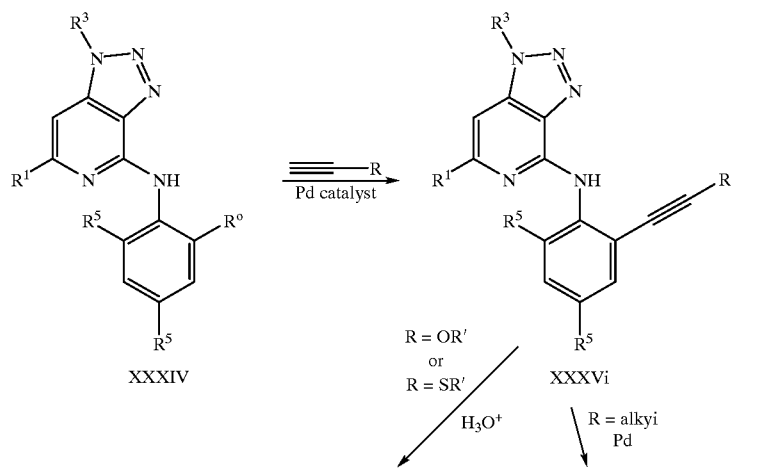

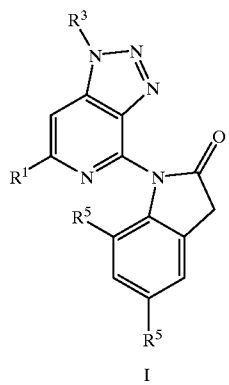

I

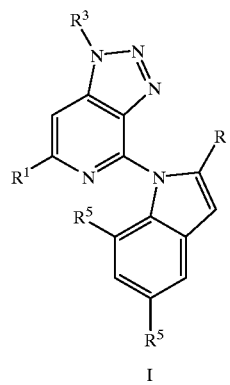

I

An alternative method for the introduction of various side chains is described in Scheme 13:

Scheme 13

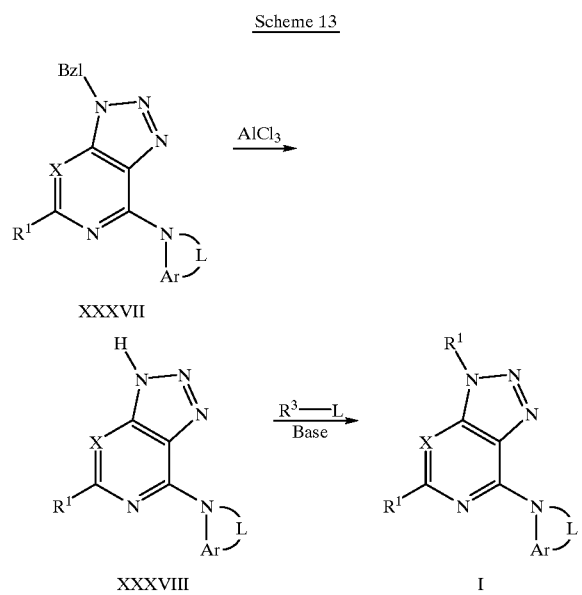

XXXVII

XXXVIII

I

The benzyltriazolopyridine or pyrimidine (XXXVII) may be synthesized by one of the previously described Schemes. The benzyl group is cleaved by the action of a strong acid or Lewis acid such as $AlCl_3$ and the resulting system of Formula (XXXVIII) is alkylated by treatment with a strong base, followed by an electrophile, or by a method described for the introduction of a functional group on a triazole by Katrinsky, A. R in *Comprehensive Heterocyclic Chemistry the Structure, Reactions Synthesis and Uses of Heterocyclic Compounds and Comprehensive Heterocyclic Chemistry II: a review of the literature, 1982–1995: the Structure, Reactions Synthesis and Uses of Heterocyclic Compounds* to give compounds of Firmula (I). Pyrazolo-, imidazolo, and indolo analogs can be synthesized in an analogous manner. Other heterocyclic linkers may be synthesized by methods described in the above references.

Other ring systems of the present invention can be synthesized according to Scheme 14:

Scheme 14

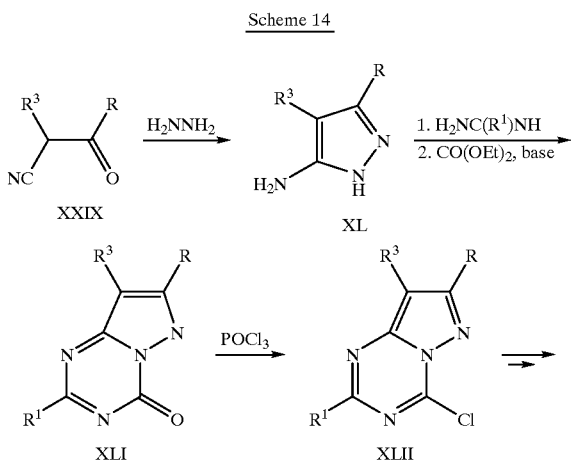

XXIX

XL

XLI

XLII

-continued

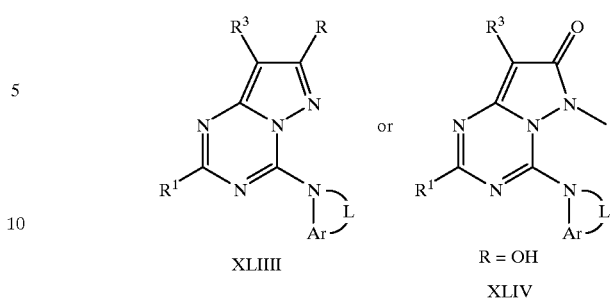

XLIIII

R = OH
XLIV

The cyano compounds of Formula (XXXIX) may be condensed with hydrazine to give compounds of Formula (XL). These may be condensed with amidines, followed by a cyclization with a carbonate in the presence of a base to give compounds of Formula (XLI). Compounds of Formula (XLI) may be converted to the chlorode (XLII) and further coupled with compounds —Ar—L—NH— to give compounds of Formula (XLIII) or (XLIV), depending on the structure of the starting compounds of Formula (XXXIX).

Another ring system of this invention may be synthesized as shown in Scheme 15.

Scheme 15

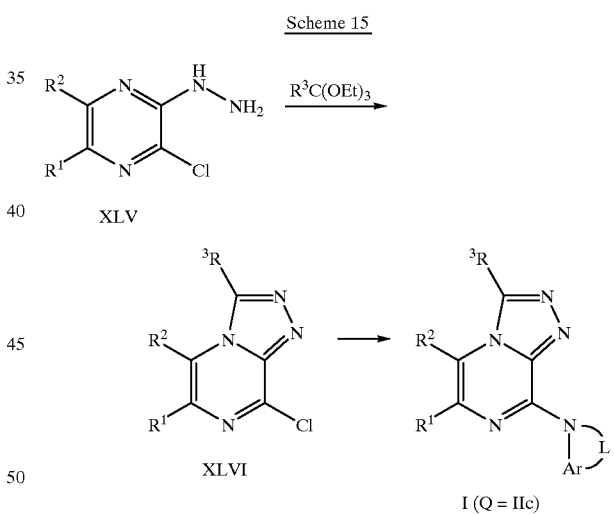

XLV

XLVI

I (Q = IIc)

The known pyrazines (see:Huynh-Dinh et. al. *J. Org. Chem.* 1979, 44, 1028) of Formula (XLV) could be converted to the fused systems of Formula (XLVI) via the action of an triethylorthoester. Compounds of Formula (XLVI) could be coupled with compounds —Ar—L—NH— to give compounds of Formula (I), (where Q is IIc).

Pyrazolopyrimidines (LI) of the present invention may be readily synthesized by following the reaction sequence outlined in Scheme 17 shown below.

Scheme 17

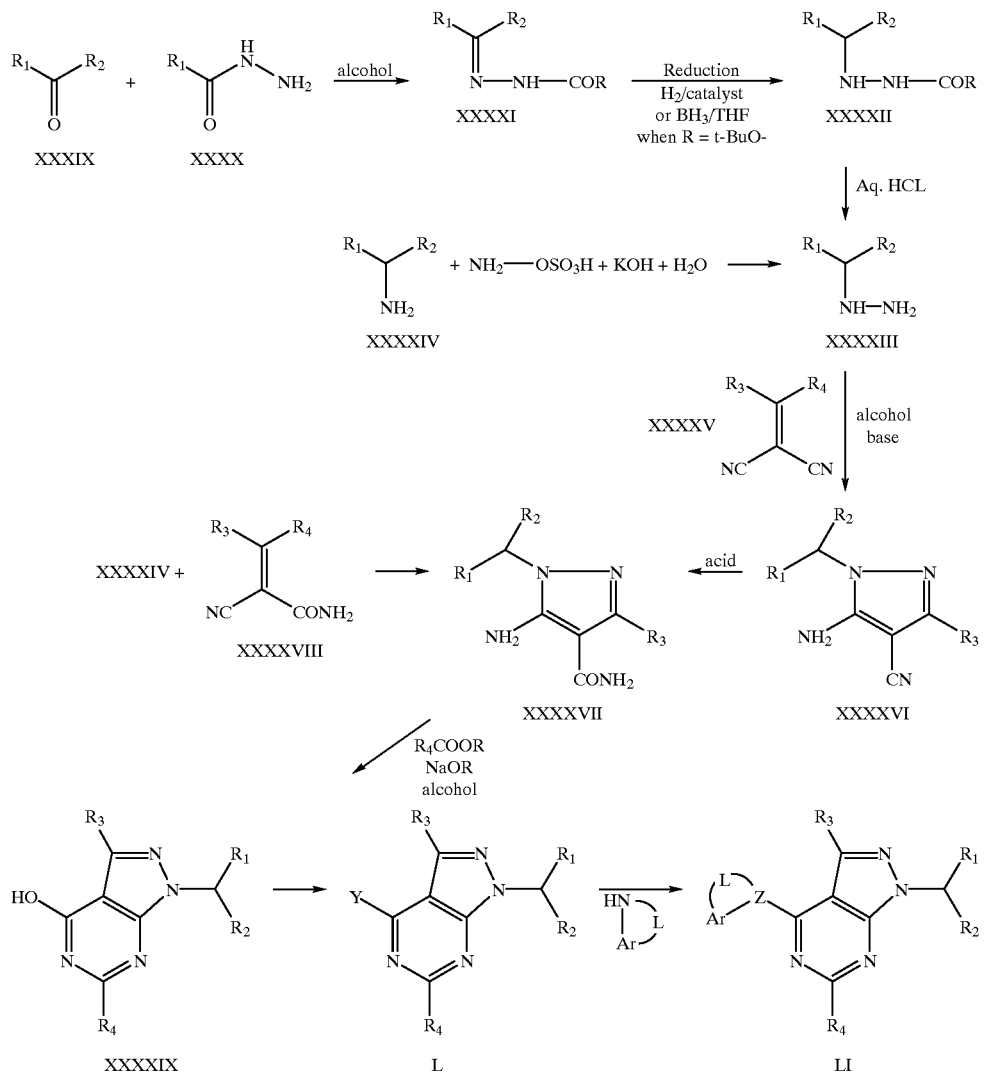

Alkylhydrazines of the type (XXXXII) were readily prepared by reacting ketone (XXXIX) with acetylhydrazide or t-butylcarbazate (XXXX) to afford hydrazone (XXXXI) which can readily be reduced using catalytic hydrogenation or by treatment with borane to give (XXXXII). XXXXII can readily be converted to XXXXIII in the presence of aq. acid (see: N. I Ghali et al J. Org. Chem. 1981, 46, 5413–14 and Boissier et al French patent M4306, 1966). Alternatively alkylhydrazines (XXXXIII) may be readily prepared from amines (XXXXIV) using hydroxylamine-O-sulfonic acid in the presence of base (See Gever et al. J. Org. Chem. 1949, 14, 813). Treatment of compound (XXXXIII) with ethylidine malononitrile (XXXXV) in alcohol medium in the presence or absence of base such as alkylamines to afford pyrazole derivative (XXXXVI). The nitrile group in the pyrazole derivative can readily be hydrolyzed using acids such as sulfuric acid, to give pyrazole carboxamide derivative (XXXXVII). Alternatively pyrazole carboxamides (XXXXVII) can be prepared by reacting (XXXXIII) with (XXXXVIII) in solvents such as alcohol in the presence of a base. Pyrazolopyrimidones of the formula (XXXXIX) can be obtained by treatment with esters in the presence of a base such as alkali metal alkoxides in refluxing alcohol (for example, see: Miyashita et al, Heterocycles, 1996, 42(2), 691). The hydroxy group of pyrazolopyrimidones (XXXXIX) can be converted to a leaving group Y (eg. tosylate, mesylate, triflate, or halogen) using classical organic group transformations to afford formula (L). Formula (L) can readily be converted to compounds of the present invention (LI) upon treatment with —Ar—L—NH— either as a neat reaction mixture at elevated temperatures or in the presence of a base in solvents such as THF, alkyl ethers or dialkylformamides.

Other ring systems can be synthesized by methods described in EP 0 778277 A1, WO 9413677 and WO 9413696.

The following examples are provided to describe the invention in further detail. These examples, which set forth the best mode presently contemplated for carrying out the invention, are intended to illustrate and not to limit the invention.

Compounds which may be prepared using the synthetic Schemes 1–14 are listed in the following Tables 1–3.

TABLE 1

4-(2,3-dihydro-1H-indol-1-yl)-1H-1,2,3-triazolo[4,5-c]pyridines and pyrimidines:

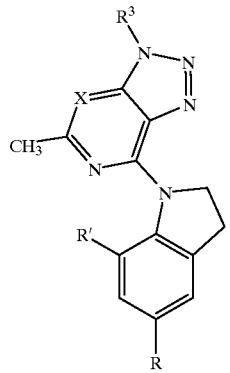

| Ex. No. | X | R₃ | R | R' | mp |
|---|---|---|---|---|---|
| 1 | CH | CH(CH₂OCH₃)C₂H₄OCH₃ | Br | Br | 136–138 |
| 2 | (S)—CH | CH(CH₂OCH₃)C₂H₄OCH₃ | Br | Br | 125–127 |
| 3 | CH | CH(Et)CH₂OCH₃ | Br | Br | 168–170 |
| 4 | CH | CH(Et)CH₂OCH₃ | Br | OCH₃ | 138–140 |
| 5 | (S)—CH | CH(CH₂OCH₃)C₂H₄OCH₃ | Br | OCH₃ | 129–131 |
| 6 | CH | CH(Et)CH₂OCH₃ | Br | Me | 147–150 |
| 7 | CH | CH(CH₂OCH₃)C₂H₄OCH₃ | Br | CHO | 124–126 |
| 8 | CH | CH(CH₂OCH₃)C₂H₄OCH₃ | Br | CH₂OH | 142–144 |
| 9 | CH | CH(CH₂OCH₃)C₂H₄OCH₃ | Br | CH₂OCH₃ | 120–122 |
| 10 | CH | CH(Et)CH₂OCH₃ | Br | Cl | 163–165 |
| 11 | CH | CH(Et)CH₂OCH₃ | OCH₃ | OCH₃ | 109–111 |
| 12 | CH | CH(CH₂OCH₃)C₂H₄OCH₃ | Br | Cl | |
| 13 | CH | CH(CH₂OCH₃)C₂H₄OCH₃ | OCH₃ | Cl | |
| 14 | CH | CH(CH₂OCH₃)C₂H₄OCH₃ | Et | Cl | |
| 15 | CH | CH(CH₂OCH₃)C₂H₄OCH₃ | Me | Cl | |
| 16 | CH | CH(CH₂OCH₃)C₂H₄OCH₃ | Cl | Cl | |
| 17 | CH | CH(Et)CH₂OCH₃ | Cl | Cl | |
| 18 | CH | CH(Et)CH₂OCH₃ | Me | Cl | |
| 19 | CH | CH(Et)CH₂OCH₃ | OCH₃ | Cl | 137–140 |
| 20 | CH | CH(Et)CH₂OCH₃ | CN | Cl | |
| 21 | CH | CH(Et)CH₂OCH₃ | SCH₃ | Cl | |
| 22 | CH | CH(Et)CH₂OCH₃ | SO₂CH₃ | Cl | |
| 23 | CH | CH(C₂H₄OMe)₂ | Cl | Cl | 119–120 |
| 24 | CH | CH(C₂H₄OMe)₂ | Br | Br | 117–118 |
| 25 | CH | CH(Et)CH₂OCH₃ | Cl | Cl | 140–142 |
| 26 | CH | CH(Et)CH₂OCH₃ | Me | Cl | |
| 27 | CH | CH(Et)CH₂OCH₃ | OCH₃ | Cl | |
| 28 | CH | CH(Et)CH₂OCH₃ | CN | Cl | |
| 29 | CH | CH(Et)CH₂OCH₃ | SMe | Cl | |
| 30 | CH | CH(Et)CH₂OCH₃ | SO₂CH₃ | Cl | |
| 31 | CH | CH(Et)₂ | Cl | Cl | 168–171 |
| 32 | CH | CH(Et)₂ | Br | Cl | 168–171 |
| 33 | CH | CH(Et)₂ | OCH₃ | Cl | 152–153 |
| 34 | CH | CH(Et)₂ | CN | Cl | 204–206 |
| 35 | CH | CH(Et)₂ | SCH₃ | Cl | 129–131 |
| 36 | CH | CH(Et)₂ | SO₂CH₃ | Cl | |
| 37 | CH | CH(Et)₂ | Br | Br | 183–186 |
| 38 | CH | CH(Et)CH₂OCH₃ | Cl | Me | |
| 39 | CH | CH₂Ph | Br | Br | 189–191 |
| 40 | CH | CH₂Ph | Cl | Cl | 205–206 |
| 41 | CH | nBu | Cl | Cl | a |
| 42 | CH | iPr | Cl | Cl | |
| 43 | CH | CH(Et)Me | Cl | Cl | |
| 44 | CH | CH₂iPr | Cl | Cl | 210–213 |
| 45 | CH | nC₅H₁₁ | Cl | Cl | 166–167 |
| 46 | CH | CH(cPr)₂ | Cl | Cl | 233–236 |
| 47 | CH | CH(nPr)₂ | Cl | Cl | 157–159 |
| 48 | N | CH(Et)CH₂OCH₃ | Br | Br | 215–217 |
| 49 | N | CH(Et)₂ | Cl | Cl | 220–221 |
| 50 | N | CH(Et)₂ | Me | Cl | |
| 51 | N | CH(Et)₂ | OCH₃ | Cl | 202–204 |
| 52 | N | CH(Et)₂ | CN | Cl | |
| 53 | N | CH(Et)₂ | SMe | Cl | |
| 54 | N | CH(Et)₂ | SO₂Me | Cl | |
| 55 | CH | CH(Et)₂ | COCH₃ | Cl | 212–214 |

TABLE 1-continued 4-(2,3-dihydro-1H-indol-1-yl)-1H-1,2,3-triazolo[4,5-c]pyridines and pyrimidines:

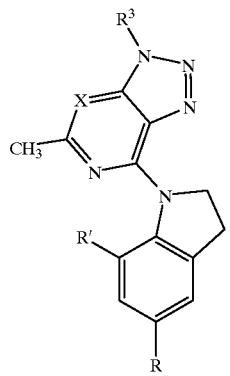

| Ex. No. | X | R₃ | R | R' | mp |
|---|---|---|---|---|---|
| 56 | CH | CH(Et)CH₂OCH₃ | Cl | Br | 151–153 |
| 57 | (R)CH | CH(Et)CH₂OCH₃ | Cl | Cl | 158–160 |
| 58 | (S)CH | CH(Et)CH₂OCH₃ | Cl | Cl | 159–162 |
| 59 | (R)CH | CH(Et)CH₂OCH₃ | OCH₃ | Cl | 150–152 |
| 60 | (S)CH | CH(Et)CH₂OCH₃ | OCH₃ | Cl | 149–151 |
| 61 | CH | CH(Et)C₂H₄OMe | Et | Cl | oil |
| 63 | CH | CH(Et)CH₂OCH₃ | Br | CF₃ | 194–196 |
| 64 | (R)CH | CH(Et)CH₂OCH₃ | OCF₃ | Cl | 74–76 |
| 65 | (S)CH | CH(Et)CH₂OCH₃ | OCF₃ | Cl | 74–76 |
| 66 | (R)CH | CH(Et)CH₂OCH₃ | Cl | OCF₃ | 149–151 |
| 67 | (S)CH | CH(Et)CH₂OCH₃ | Cl | OCF₃ | 150–151 |
| 68 | CH | CH(Et)CH₂CN | Cl | Cl | 194–196 |
| 69 | N | CH(Et)nPr | Cl | Cl | 213–215 |
| 70 | N | CH(CH₃)nPr | Cl | Cl | 165–167 |
| 71 | N | CH(nPr)₂ | Cl | Cl | 209–212 |
| 72 | N | CH(Et)CH₂OCH₃ | Cl | Cl | 204–206 |
| 73 | N | CH(Et)nPr | OCH₃ | Cl | 213–215 |
| 74 | N | CH(Et)CH₂OCH₃ | OCH₃ | Cl | 162–163 |
| 75 | CH | CH(Et)C₂H₄OCH₃ | OCH₃ | Cl | 131–132 |
| 76 | CH | CH(Et)CH₂cPr | Cl | Cl | 151–152 |
| 77 | CH | CH(Et)₂ | OCH₃ | CH₃ | 148–149 |
| 78 | CH | CH(Et)CH₂cPr | OCH₃ | Cl | 90–92 |
| 79 | CH | CH(CH₂OCH₃)CH₂cPr | Cl | Cl | 138–140 |
| 80 | CH | CH(CH₂OCH₃)CH₂cPr | OCH₃ | Cl | 107–109 |
| 81 | CH | CH(Et)₂ | Cl | Br | 166–167 |
| 82 | CH | CH(Et)₂ | Cl | OCH₃ | 152–154 |
| 83 | CH | CH(CH₃)Et | Cl | Cl | 158–160 |
| 84 | CH | CH(CH₃)nPr | Cl | Cl | 177–179 |
| 85 | CH | CH(Et)₂ | Br | H | 161–163 |
| 86 | CH | CH(Et)CO₂CH₃ | Cl | Cl | 217–218 |
| 87 | (R)CH | CH(Et)CH₂OCH₃ | Br | Cl | 161–164 |
| 88 | (S)CH | CH(Et)CH₂OCH₃ | Br | Cl | 161–164 |
| 89 | (S)CH | CH(Et)CH₂OCH₃ | Et | Cl | 115–116 |
| 90 | (S)CH | CH(Et)CH₂OCH₃ | CH₃ | Cl | 166–169 |
| 91 | CH | CH(CH₃)cPr | Cl | Cl | 170–172 |
| 92 | CH | CH(CH₃)cPr | OCH₃ | Cl | 137–141 |
| 93 | CH | CH(Et)nPr | Cl | Cl | 153–156 |
| 94 | CH | CH(Et)nPr | OCH₃ | Cl | 122–125 |
| 95 | CH | CH(CH₃)Et | OCH₃ | Cl | 102–105 |
| 96 | CH | CH(Et)CH₂(1,2,4-triazole) | Cl | Cl | 199–202 |
| 97 | CH | CH(CH₃)nPr | OCH₃ | Cl | 158–161 |
| 98 | CH | CH(Et)CH₂Oallyl | Cl | Cl | 112–114 |
| 99 | CH | CH(Et)CH₂Oallyl | OCH₃ | Cl | amorphous |
| 100 | CH | CH(Et)CH₂Obenzyl | Cl | Cl | 108–109 |
| 101 | CH | CH(Et)CH₂OH | Cl | Cl | 175–178 |
| 102 | CH | CH(Et)CH₂(1,2,3,5-tetrazole) | Cl | Cl | 203–206 |
| 103 | CH | CH(Et)CH₂OEt | Cl | Cl | 133–135 |
| 104 | CH | CH(Et)CH₂OcPr | Cl | Cl | 113–115 |

TABLE 2

4-(1-H-indol-1-yl)-1H-1,2,3-triazolo[4,5-c]pyridines and pyrimidines:

| Ex. No. | X | $R_3$ | R | R' | mp |
|---|---|---|---|---|---|
| 151 | CH | CH(Et)CH$_2$OMe | Br | OMe | |
| 152 | CH | CH(Et)CH$_2$OCH$_3$ | Br | Me | |
| 153 | CH | CH(Et)CH$_2$OCH$_3$ | Cl | Cl | |
| 154 | CH | CH(CH$_2$OMe)C$_2$H$_4$OMe | Br | Cl | |
| 155 | CH | CH(CH$_2$OMe)C$_2$H$_4$OMe | OMe | Cl | |
| 156 | CH | CH(CH$_2$OMe)C$_2$H$_4$OMe | Cl | Cl | |
| 157 | CH | CH(Et)$_2$ | Cl | Cl | |
| 158 | CH | CH(Et)$_2$ | Me | Cl | |
| 159 | CH | CH(Et)$_2$ | OMe | Cl | |
| 160 | CH | CH(Et)$_2$ | CN | Cl | |
| 161 | CH | CH(Et)$_2$ | SMe | Cl | |
| 162 | CH | CH(Et)$_2$ | SO$_2$Me | Cl | |
| 163 | CH | CH(C$_2$H$_4$OMe)$_2$ | Cl | Cl | |
| 164 | CH | CH(C$_2$H$_4$OMe)$_2$ | Me | Cl | |
| 165 | CH | CH(Et)C$_2$H$_4$OMe | Cl | Cl | |
| 166 | CH | CH(Et)C$_2$H$_4$OMe | Me | Cl | |
| 167 | CH | CH(Et)C$_2$H$_4$OMe | OMe | Cl | |
| 168 | CH | CH(Et)C$_2$H$_4$OMe | CN | Cl | |
| 169 | CH | CH(Et)C$_2$H$_4$OMe | SMe | Cl | |
| 170 | CH | CH(Et)C$_2$H$_4$OMe | SO$_2$Me | Cl | |
| 171 | CH | CH(Et)$_2$ | Cl | Cl | |
| 172 | CH | CH(Et)$_2$ | Me | Cl | |
| 173 | CH | CH(Et)$_2$ | OMe | Cl | |
| 174 | CH | CH(Et)$_2$ | CN | Cl | |
| 175 | CH | CH(Et)$_2$ | SMe | Cl | |
| 176 | CH | CH(Et)$_2$ | SO$_2$Me | Cl | |
| 177 | CH | CH(CH$_2$OMe)C$_2$H$_4$OMe | Me | Me | |
| 178 | CH | CH(Et)CH$_2$OCH$_3$ | Cl | Me | |
| 179 | N | CH(Et)CH$_2$OCH$_3$ | Br | Br | |
| 180 | CH | CH(Et)$_2$ | Cl | Cl | |
| 181 | CH | CH(Et)$_2$ | Me | Cl | |
| 182 | CH | CH(Et)$_2$ | OMe | Cl | |
| 183 | CH | CH(Et)$_2$ | CN | Cl | |
| 184 | CH | CH(Et)$_2$ | SMe | Cl | |
| 185 | CH | CH(Et)$_2$ | SO$_2$Me | Cl | |
| 186 | CH | CH(Et)CH$_2$OCH$_3$ | Br | Br | amorphous |

TABLE 3

1,2,3,4-tetrahydro-1H-1,2,3-triazolo[4,5-c]pyridin-4-yl and pyrimidin-4-yl quinolines

| Ex. No. | X | $R_3$ | R | R' | Y | mp |
|---|---|---|---|---|---|---|
| 286 | CH | CH(Et)CH$_2$OMe | Me | H | CH$_2$ | 126–128 |
| 287 | CH | CH(Et)CH$_2$OMe | Me | Br | CH$_2$ | 111–113 |
| 288 | CH | CH(Et)CH$_2$OMe | Me | Cl | CH$_2$ | 110–112 |
| 289 | CH | CH(CH$_2$OMe)C$_2$H$_4$OMe | Me | Cl | CH$_2$ | 107–109 |
| 290 | CH | CH(Et)CH$_2$OMe | Me | Br | O | 105–107 |
| 291 | CH | CH(Et)$_2$ | Me | Cl | | |
| 292 | CH | CH(Et)$_2$ | Me | Cl | | |

The compound of Example 400 and the other compounds listed shown in Table 4 were prepared using the synthetic procedure of Scheme 17 and the reaction conditions outlined in Example 400.

TABLE 4

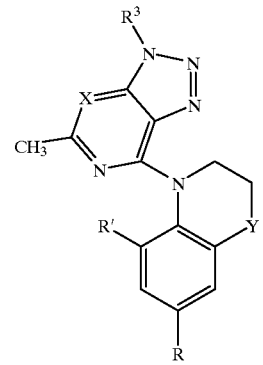

| Ex. No. | $R_1$ | $R_2$ | $R_3$ | X | mp (° C.) |
|---|---|---|---|---|---|
| 400 | CH(Et)$_2$ | Br | Br | Me | 190–191 |
| 401 | CH(Et)$_2$ | Cl | Cl | Me | 164–166 |
| 402 | CH(Et)C≡CH | Cl | Cl | Me | 82–84 |
| 403 | CH(Et)$_2$ | Br | Br | H | 191–192 |
| 404 | CH(Et)$_2$ | Cl | Cl | H | 180–181 |
| 405 | CH(Me){(CH$_2$)$_2$—Me} | Cl | Cl | Me | 131–132 |
| 406 | CH(Me){(CH$_2$)$_2$—Me} | Cl | Br | Me | 138–140 |
| 407 | CH(Me){(CH$_2$)$_2$—Me} | Br | Br | Me | 147–149 |
| 408 | CH(Me){(CH$_2$)$_2$—Me} | H | OMe | Me | 133–135 |
| 409 | CH(Me){(CH$_2$)$_2$—Me} | Cl | OMe | Me | 115–117 |
| 410 | CH(Et)$_2$ | Cl | OMe | Me | 162–163 |
| 411 | CH(Me){(CH$_2$)$_2$—Me} | H | Cl | Me | 103–105 |
| 412 | CH(Me){(CH$_2$)$_3$—OMe} | Cl | Cl | Me | oil |
| 413 | CH(Me){(CH$_2$)$_2$—Me} | H | Br | Me | 107–109 |
| 414 | benzyl | Cl | Cl | Me | 145–146 |

EXAMPLE 1

Preparation of (S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyridine Part A:

L-Dimethyl aspartate hydrochloride (5 g, 25.3 mmol) and triphenylmethyl chloride (7.65 g, 27.5 mmol) were suspended in dry $CH_3CN$ (50 mL) at 0° C. To that $Et_3N$ (4.5 mL, 32.3 mmol) was added dropwise, followed by N-methylmorpholine (2.5 mL, 27.5 mmol). The mixture was stirred at 0° C. for 1 h and at 25° C. for 30 min. Then it was partitioned between EtOAc (200 mL) and water (50 mL) and the organic extract was washed with water (50 mL), brine (50 mL), dried ($MgSO_4$) and stripped in vacuo. The product, diethyl N-triphenylmethyl aspartate, was >90% clean by NMR analysis.

NMR($CDCl_3$)δ 7.16–7.51 (m, 15 H), 3.68 (s, 3H), 3.66–3.74 (m, 1H), 3.26 (s, 3H), 2.93 (d, 1H, J=9.9 Hz), 2.63–2.69 (dd, 1H, $J_1$=14.6, $J_2$=5.1 Hz), 2.48–2.55 (dd, 1H, $J_1$=14.6 Hz, $J_2$=7 Hz).

Part B:

(S)-Diethyl N-triphenylmethyl aspartate (~25 mol) was dissolved in dry THF (150 mL) and cooled to 0° C. To that a 1 M solution of $LiAlH_4$ in THF (50 mL, 50 mmol) was added dropwise and the reaction was stirred for 2 h and allowed to warm to 25° C. Then it was cooled and quenched with water (5 mL) and 1 N NaOH (4 mL), diluted with ether (200 mL) and the precipitated solids were filtered off. The filtrate was concentrated in vacuo to give the product, 2-N-triphenylamino-1,4-butane diol (>90% clean by NMR analysis).

NMR($CDCl_3$)δ 7.17–7.57 (m, 15H), 3.68–3.77 (m, 1H), 3.56–3.63 (m, 1H), 3.19 (d, 1H, J=8.8 Hz), 2.76–2.86 (m, 2H), 2.2–2.7 (br, 3H), 1.54–1.63 (m, 1H), 1.36–1.54 (m, 1H).

Part C:

(S)-2-N-triphenylamino-1,4-butane diol (-25 mmol) dissolved in dry THF (50 mL) was added into a suspension of NaH 60% in oil (2.34 g, 58.5 mmol) in dry THF (50 mL) at 0° C., and the mixture was stirred at 9° C. for 30 min and at 25° C. for 1 h. Then it was cooled in an ice bath and $CH_3I$ (3.6 mL, 58.5 mmol) was added dropwise. The reaction was stirred at 0° C. for 30 min and at 25° C. for 2 h, the excess NaH was quenched with water and the THF was stripped off. The residue was partitioned between EtOAc (200 mL) and water (50 mL) and the organic extract was washed with water (50 mL), brine (50 mL), dried ($MgSO_4$) and stripped in vacuo. The product, 2-N-triphenylamino-1,4-dimethoxy butane was >90% clean by NMR analysis.

NMR($CDCl_3$)δ 7.15–7.59 (m, 15 H), 3.34–3.41 (m, 1H), 3.22 –3.30 (m, 1H), 3.24 (s, 3H), 3.03 (s, 3H), 2.86 (dd, 1H, $J_1$=9.5 Hz, $J_2$=3.3 Hz), 2.65–2.75 (m, 1H), 2.4–2.46 (br, 1H), 2.30–2.35 (m, 1H), 2.57–2.8 (m, 2H).

Part D:

(S)-2-N-Triphenylamino-1,4-dimethoxy butane (-25 mmol) was dissolved in a mixture of $CH_2Cl_2$ (100 mL) and methanol (50 mL) and 1 M HCl in ether was added (50 mL). The reaction was stirred at 25° C. for 16 h, the solvent was stripped off and the residue was washed with 1:1 ether/hexane (3×50 mL). The remaining oil, 2-amino-1,4-dimethoxybutane hydrochloride, was dried under vacuum (3.87 g, 88%).

NMR($CDCl_3$)δ 8.2–8.5 (br, 3H), 3.5–3.7 (m, 5H), 3.41 (s, 3H), 3.36 (s, 3H), 2.05–2.2 (m, 1H), 1.90–2.01 (m, 1H).

Part E:

4—Chloro-6-methyl-3-nitropyridone:

4-Hydroxy-6-methyl-3-nitropyridone (4.0 g, 23,52 mmol) was treated with cyclohexylamine (2.8 mL, 24.46 mmol) in MeOH (50 mL) until all dissolved. The MeOH was stripped in vacuo and the resulting salt was dried and treated with $POCl_3$ (30 mL) at 25° C. for 30 h. The reaction was then poured into ice/water (400 mL) and extracted with EtOAc (2×200 mL). The combined EtOAc extracts were washed with water (100 mL), 1 N NaOH (20 mL), water (100 mL) and brine, dried ($MgSO_4$) and stripped in vacuo. The residue was washed with 20% EtOAc/hexanes (2×30 mL) to give the product (2.9 g).

Part F:

(S)-6-Methyl-3-nitro-4-(1-methoxymethyl-3-methoxypropylamino) pyridone:

1-methoxymethyl-3-methoxypropylamine (4.19 g, 22.3 mmol), and 4-chloro-6-methyl-3-nitropyridone (3.87 g, 22.3 mmol) were mixed in $CH_3CN$ (70 mL) and diisopropylethylamine (9.4 mL, 53.6 mmol) was added. The reaction was stirred at 25° C. for 16 h and at reflux for 2.5 h. The solvent was stripped off and the residue was dissolved in $CH_2Cl_2$ (150 mL) and the $CH_2Cl_2$ was washed with water (80 mL). The water was extracted with $CH_2Cl_2$ (50 mL) and the combined organic extracts were dried ($MgSO_4$) and stripped in vacuo. The residue was crystallized from EtOAc and washed with 40% EtOAc/hexanes to give the product, (4.8 g, 75%).

NMR(DMSO)δ 9.13 (d, 1H, J=8.8 Hz), 5.9 (s, 1H), 3.92–4.02 (m, 1H), 3.20–3.25 (m, 2H), 3.28–3.4 (m, 2H), 3.25 (s, 3H), 3.18 (s, 3H), 2.09 (s, 3H), 1.65–1.90 (m, 2H).

Part G:

(S)-2—Chloro-6-methyl-3-nitro-N-(1-methoxymethyl-3-methoxypropyl)pyridin-4-amine:

4-[3-(1,4-dimethoxybutyl)amino]-6-methyl-3-nitropyridone (4.8 g, 16.82 mmol) was dissolved in $POCl_3$ (50 mL) and stirred at 25° C. for 40 h. Then the reaction was poured into ice/water (500 mL), allowed to react, neutralized with solid $NaHCO_3$ after EtOAc was added (150 mL) and extracted with EtOAc (2×300 mL). The EtOAc was dried ($MgSO_4$) and stripped in vacuo to give the product.

NMR ($CDCl_3$)δ 7.08 (d, 1H, J=7.7 Hz), 6.65 (s, 1H), 3.85–3.95 (m, 1H), 3.30–3.50 (m, 4H), 3.38 (s, 3H), 3.33 (s, 3H), 2.43 (s, 3H), 1,80–2.02 (m, 2H).

Part H:

(S)-3-amino-2-chloro-4-N-(1-methoxymethyl-3-methoxypropyl)-6-methyl-pyridin-4-amine:

2—Chloro-6-methyl-3-nitro-N-(1-methoxymethyl-3-methoxypropyl)pyridin-4-amine (~16.82 mmol) was heated at reflux with Fe powder (10 g) in methanol (120 mL) in the presence of glacial acetic acid (10 mL) for 2 h. Then the iron was filtered through celite, the celite was washed with methanol(80 mL) and the filtrate was stripped in vacuo. The residue was dissolved in 10% HCl (120 mL) and EtOAc was added (160 mL). The mixture was neutralized with solid NaHCO$_3$ and the aqueous layer was extracted with EtOAc (2×100 mL). The combined organic extracts were washed with brine (50 mL), dried (MgSO$_4$) and stripped in vacuo (4.1 g).

NMR(CDCl$_3$)&δ 6.4 (s, 1H), 5.2–5.35 (br s, 1H), 3.70–3.80 (m, 1H), 3.2–3.8 (m, 6H), 3.38 (s, 3H), 3.33 (s, 3H), 2.42 (s, 3H), 1.8–2.0 (m, 2H).

Part I:

(S)-4-chloro-1-(1-methoxymethyl-3-methoxypropyl)-6-methyl-1H-1,2,3-triazolo[4,5-c]pyridine:

3-amino-2-chloro-6-methyl-4-N-(1-methoxymethyl-3-methoxypropyl)pyridin-4-amine (4.1 g, 14.98 mmol) was dissolved in a mixture of CH$_2$Cl$_2$ (40 mL) and 50% acetic acid (40 mL) and cooled to 0 ° C. in an ice bath. To that a solution of NaNO$_2$ (1.84 g, 26.86 mmol) in water (10 mL) was added dropwise and the reaction was stirred at 0° C. for 30 min and at 25° C. for 1.5 h. Then the acetic acid was neutralized with solid NaHCO$_3$ and water (80 mL) was added. The mixture was extracted with EtOAc (2×100 mL) and the combined organic extracts were combined and washed with brine (50 mL), dried and stripped in vacuo. The residue was chromatographed on silica gel (40% EtOAc/hexanes eluent) to give the product (4.05 g, 56% overall for the eight steps).

NMR(CDCl$_3$)δ 7.25 (s, 1H), 5.04–5.13 (m, 1H), 3.98 (dd, 1H, J$_1$=9.9 Hz, J$_2$=8.4 Hz), 3.84 (dd, 1H, J$_1$=10.2 Hz, J$_2$=4.4 Hz), 3.39 (dt, 1H, J$_1$=9.9 Hz, J$_2$=4.8 Hz), 3.25 (s, 3H), 3.17 (s, 3H), 2.91 (dt, 1H, J$_1$=9.5 Hz, J$_2$=4.0 Hz), 2.68 (s, 3H), 2.22–2.6 (m, 2H).

Part J:

(S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyridine (S)-4-chloro-1-(1-methoxymethyl-3-methoxypropyl)-6-methyl-1H-1,2,3-triazolo[4,5-c]pyridine (0.72 g, 2.54 mmol) and 5,7-dibromoindoline (0.72 g, 2.60 mmol) were dissolved in anhydrous THF (6 mL) and cooled in an ice bath. To that a 1 M solution of NaHMDS in THF (3.0 mL, 3.0 mmol) was added and the reaction was stirred for 20 min, allowed to warm to 25° C. and stirred for 3 h. Then water (30 mL) was added and the mixture was extracted twice with EtOAc (80 and 40 mL). The combined organic extracts was washed with brine (30 mL) dried (MgSO$_4$) and stripped in vacuo. The residue was chromatographed on silica gel using 40% EtOAc/hexanes as eluent to give the product (1.14 g, 85% yield).

Elemental analysis. Theory: C, 45.73; H, 04.41; N, 13.33; Found: C, 45.99; H, 4.25; N, 13.37.

EXAMPLE 2

Preparation of (R,S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyridine Part A:

(R, S)-2-Aminobutyrolactone hydrobromide (8.0 g, 44 mmol) and triphenylmethyl chloride (12.8 g, 46 mmol) were suspended in dry CH$_3$CN (80 mL) at 25° C. To that Et$_3$N (13.6 mL, 100 mmol) was added dropwise, the reaction mixture was stirred at 25°C. for 4 h and partitioned between EtOAc (120 mL) and water (50 mL). The organic layer was washed with water (50 mL), brine (50 mL), dried (MgSO$_4$) and stripped in vacuo. The residue was recrystallized from EtOAc/hexanes to give 2-triphenylmethylamino-butyrolactone (10.5 g).

Part B:

Lithium aluminum hydride (1.4 g, 36 mmol) was suspended in dry THF (50 mL) and cooled to 0° C. in an ice bath. To that a solution of 2-triphenylmethylamino-butyrolactone (11 g, 31.9 mmol) in dry THF (70 mL) was added dropwise over a period of 20 min. After the addition was over the reaction mixture was stirred at 00° C. for 1 h, at 25° C. for 3 h and quenched by the sequential addition of water (2 mL) 1 N NaOH (2 mL) and water (3 mL), and diluted with ether (150 mL). The precipitated solids were filtered off and the filtrate was concentrated in vacuo to give (R,S)-2-N-triphenylamino-1,4-butanediol. This was used in the same synthetic scheme as previously described for the chiral material (Example 414, Parts C–J) to obtain the racemic material. Elemental analysis. Theory: C, 45.73; H, 04.41; N, 13.33; Br, 30.43; Found: C, 46.11; H, 4.10; N, 13.28; Br, 30.59.

EXAMPLE 3

Preparation of (R,S)-4-(5,7-dibromo-2,3-dihydro-1H-indol-1-yl)-1-[1-(methoxymethyl)propyl]-6-methyl-1H-1,2,3-triazolo[4,5-c]pyridine (R, S)-4-chloro-1-(1-methoxymethylpropyl)-6-methyl-1H-1,2,3-triazolo[4,5-c]pyridine (508 mg, 2.0 mmol) and 5,7-dibromoindoline (554 mg, 2.0 mmol) were dissolved in anhydrous THF (5 mL) and cooled in an ice bath. To that a 1 M solution of NaHMDS in THF (2.0 mL, 2.0 mmol) was added and the reaction was stirred for 20 min, allowed to warm to 25° C. and stirred for 20 h. An additional 0.6 mL (0.6 mmol) NaHMDS was added and the reaction was stirred for 4 H. Then water (30 mL) was added and the mixture was extracted with EtOAc (100 mL). The organic extract was washed with brine (30 mL) dried (MgSO$_4$) and stripped in vacuo. The residue was chromatographed on silica gel using 30% EtOAc/hexanes as eluent to give the product (0.7 g, 79%).

EXAMPLE 4

Preparation of (R,S)-4-(5-bromo-7-methoxy-2,3-dihydro-1H-indol-1-yl)-1-[1-(methoxymethyl)propyl]-6-methyl-1H-1,2,3-triazolo[4,5-c]pyridine (R,S)-4-(5,7-dibromo-2,3-dihydro-1H-indol-1-yl)-1-[1-(methoxymethyl)propyl]-6-methyl-1H-1,2,3-triazolo[4,5-]pyridine (0.4 g, 0.9 mmol) was heated to reflux in DMF (5 mL) with NaOMe/MeOH 25% w/w (0.2 mL, ~1 mmol) and CuBr (14.3 mg, 0.1 mmol) for 2 h. Then the reaction mixture was partitioned between EtOAc (100 mL), and water (30 mL). The organic extract was washed with water (30 mL)), brine (30 mL), dried (MgSO4) and stripped in vacuo. The residue was chromatographed on silica gel using 30% EtOAc/hexanes as eluent to give the product (180 mg, 45%). Elemental analysis. Theory: C, 53.82; H, 5.429; N, 15.69; Found: C, 53.73; H, 5.14; N, 15.54.

EXAMPLE 5

Preparation of (R,S)-4-(5-bromo-7-methoxy-2,3-dihydro-1H-indol-1-yl)-1-[1-(methoxymethyl)-3-methoxypropyl]-6-methyl-1H-1,2,3-triazolo[4,5-c] pyridine Synthesized under similar conditions described in Example 2. Elemental analysis. Theory: C, 52.95; H, 05.50; N, 14.70; Br, 16.77; Found: C, 53.28; H, 5.52; N, 14.63; Br 16.65.

EXAMPLE 6

Preparation of (R,S)-4-(5-bromo-7-methyl-2,3-dihydro-1H-indolyl)-1-[1-(methoxymethy)lpropyl-6-methyl-1H-1,2,3-triazolo[4,5-c]pyridine (R,S)-4-(5,7-dibromo-2,3-dihydro-1H-indol-1-yl)-1-[1-(methoxymethyl)propyl]-6-methyl-1H-1,2,3-triazolo[4,5-c] pyridine (0.7 1.41 mmol) was dissolved in anhydrous THF (5 mL) and cooled to −78° C. A 1.6 M solution of n-butyllithium was added dropwise, the reaction was stirred for 5 min and MeI (0.1 mL, 1.61 mmol) was added. The reaction was stirred at −78° C. for 30 min, allowed to warm to 25° C., quenched with water (30 mL), and extracted with EtOAc (90 mL). The organic extract was washed with brine (30 mL), dried ($MgSO_4$) and stripped in vacuo. The residue was chromatographed on silica gel using 40% EtOAc/hexanes as eluent to give the product (430 mg, 71%). Elemental analysis: Theory: C, 55.82; H, 05.62; N, 16.27; Br, 18.57; Found: C, 56.09; H, 5.39; N, 16.27; Br, 18.78.

EXAMPLE 7

Preparation of (R,S)-4-(5-bromo-7-formyl-2,3-dihydro-1H-indolyl)-1-[1-(methoxymethyl)-3-methoxypropyl]-6-methyl-1H-1,2,3-triazolo[4,5-cl pyridine (R,S)-4-(5,7-dibromo-2,3-dihydro-1H-indol-1-yl)-1-[1-(methoxymethyl)propyl]-6-methyl-1H-1,2,3-triazolo[4,5-c] pyridine by treatment with nBuLi as described in Example 6 and reaction with DMF. Elemental analysis. Theory: C, 53.17; H, 5.109; N, 14.76; Found: C, 53.57; H, 5.02; N, 14.64.

EXAMPLE 8

Preparation of (R,S)-4-(5-bromo-7-hydroxymethyl-2,3-dihydro-1H-indolyl)-1-[1-(methoxymethyl)-3-methoxypropyl]-6-methyl-1H-1,2,3-triazolo[4,5-c] pyridine (R,S)-4-(5-bromo-7-formyl-2,3-dihydro-1H-indolyl)-1-[1-(methoxymethyl)-3-methoxypropyl]-6-methyl-1H-1,2,3-triazolo[4,5-c]pyridine (460 mg, 0.97 mmol) was dissolved in absolute ethanol (10 mL) and cooled in an ice bath. Then NaBH4 was added (40 mg, 1.0 mmol) and the reaction was stirred at 0° C. for 15 min and at 25° C. for 2 h. The reaction was quenched with 0.3 N NaOH (30 mL) and extracted with EtOAc (100 mL). The organic extract was washed with brine (30 mL), dried ($MgSO_4$) and stripped in vacuo. The residue was chromatographed on silica gel using 66% EtOAc/hexanes as eluent to give the product 380 mg, 82%). Elemental analysis. Theory: C, 52.95; H, 05.50; N, 14.70; Found: C, 53.14; H, 5.45; N, 14.39.

EXAMPLE 9

Preparation of (R,S)-4-(5-bromo-7-methoxymethyl-2,3-dihydro-1H-indolyl)-1-[1-(methoxymethyl)-3-methoxypropyl]-6-methyl-1H-1,2,3-triazolo[4,5-c] pyridine (R,S)-4-(5-bromo-7-hydroxymethyl-2,3-dihydro-1H-indolyl)-1-[1-(methoxymethyl)-3-methoxypropyl]-6-methyl-1H-1,2,3-triazolo[4,5-c]pyridine (220 mg, 0.47 mmol), dissolved in anhydrous THF (4 mL) was treated with NaH 60% in oil (23 mg, 0.56 mmol) at 25° C. for 15 min and MeI (0.035 mL, 0.56 mmol) was added. The reaction was stirred at 25° C. for 16 h and partitioned between EtOAc (90 mL) and water (30 mL). The organic extract was washed with brine (30 mL), dried ($MgSO_4$) and stripped in vacuo. The residue was chromatographed on silica gel using 50% EtOAc/hexanes as eluent to give the product 190 mg, 85%). Elemental analysis. Theory: C, 53.88; H, 5.765; N, 14.28; Found: C, 54.09; H, 5.69; N, 13.95.

EXAMPLE 10

Preparation of (R,S)-4-(5-bromo-7-chloro-2,3-dihydro-1H-indolyl)-1-[1-(methoxymethy)lpropyl-6-methyl-1H-1,2,3-triazolo[4,5-cl pyridine Part A:

1-Acetyl-5-bromoindoline (2.47 g, 10.29 mmol) was heated at reflux with N-chlorosuccinimide (1.56 g, 10.40 mmol) in $CH_3CN$ for 30 min and an additional amount NCS (1 g, 7.47 mmol) was added while hot and the reaction was stirred at 25° C. for 16 h. The solvent was stripped in vacuo and the residue was chromatographed on silica gel using 20% EtOAc/hexanes as eluent to give 1-acetyl-5-bromo-7-chloroindoline (1.17 g).

Part B:

1-acetyl-5-bromo-7-chloroindoline (1.17 g) was dissolved in a mixture of ethanol (15 mL) and water (8 mL) containing KOH (0.5 g) and heated to reflux for 2 h. The reaction was partitioned between EtOAc (100 mL) and water (20 mL). The organic extract was washed with brine (20 mL), dried and stripped in vacuo to give 5-bromo-7-chloroindoline (0.87 g).

Part C:

5-bromo-7-chloroindoline (0.465 g) was coupled with (R,S)-4-chloro-1-(1-methoxymethylpropyl)-6-methyl-1H-1,2,3-triazolo[4,5-c]pyridine (0.5 g) using NaHMDS as described in Example 3 to give the product (0.42 g) after chromatographic purification (30% EtOAc/hexanes).

EXAMPLE 48

Preparation of (R,S)-4-(5,7-dibromo-2,3-dihydro-1H-indol-1-yl)-1-[1-methoxyethyl)propyl]-6-methyl-1H-1,2,3-triazolo[4,5-c] pyrimidine Part A:

4,6-Dihydroxy-2-methylpyrimidine (60 g) was added in portions to fuming nitric acid (120 mL) at 0° C. while cooling the reaction flask. After completion of addition, the reaction was stirred an additional 1 h at 0° C. followed by another 1 h at room temperature. The reaction mixture was then poured over ice (200 g) and the ice was allowed to melt. A light pink solid was isolated by filtration and washed with cold water (100 mL). The solid was dried in a vacuum oven overnight to yield 4,6-dihydroxy-2-methyl-5-nitropyrimidine (72.5 g).

Part B:

The product of Part A was added portionwise to phosphorous oxychloride (400 mL) under a nitrogen atmosphere followed by dropwise addition of N,N-diethylaniline (80 mL). The reaction mixture was refluxed for 2½ h with stirring, cooled to room temperature, poured over ice (2.0 Kg) and stirred for 1 hr. The aqueous layer was extracted with diethyl ether (4×500 mL) and the extracts combined.

The combined extracts were washed with brine (500 mL), dried over anhydrous magnesium sulfate, filtered and stripped down to afford 4,6-dichloro-2-methyl-5-nitropyrimidine as a yellow solid (68.8 g) which has an unpleasant odor.

Part C:

The product of Part B (42 g) was added to acetic acid (77 mL) and methanol (350 mL). To this mixture was added iron powder (42 g) in portions, stirred for 2 h at 60–65 C, cooled to room temperature, and filtered. The filtrate was stripped to a brown solid, which was extracted with ethyl acetate (2×500 mL), washed with 1N NaOH (250 mL), and brine (500 mL). The organic layer was dried over anhydrous magnesium sulfate, filtered and stripped down to yield 5-amino-4,6-dichloro-2-methylpyrimidine as a pale yellow solid (25.4 g).

Part D:

The product of Part C (3.6 g) from was dissolved in ethanol (40 mL) and N,N- diisopropylethylamine (3.1 g). To this mixture 2-amino-1-methoxy-butane (3.5 g) was added and refluxed for 7 days. The ethanol was stripped off in vacuum, the residue was partitioned between ethyl acetate (50 mL) and water (50 mL). The organic layer was stripped down to yield 5-amino-4-chloro-6-(1-methoxy-2-butyl) amino-2-methylpyrimidine as an orange yellow solid (4.7 g; mp 128–130 C).

Part E:

The product of Part D (3.1 g) was dissolved in dichloromethane (25 mL) and 50% aqueous acetic acid (25 mL). To this stirred mixture was added sodium nitrite (0.92 g) in water (5 mL) dropwise at room temperature. After completion of addition, the reaction was stirred for an additional 15 min. The organic layer was separated, washed with water, dried with anhydrous magnesium sulfate, and stripped down to a residue. The residue was purified by flash column chromatography ($CH_2Cl_2$) to afford 7-chloro-3-[1-(1-methoxymethyl)propyl)-5-methyl-3H-1,2,3-triazolo[4,5-d] pyrimidine as a white crystalline solid (3.1 g; 86–87 C). Elemental analysis for $C_{10}H_{14}ClN_5O$: Theory C: 46.97, H: 5.53, N: 27.39. Found: C: 47.22 , H:5.43, N: 27.47.

Part F:

7-chloro-3-[1-(1-methoxymethyl)propyl]-5-methyl-3H-1,2,3-triazolo[4,5-d]-pyrimidine (210 mg, 0.82 mmol) was heated with 5,7-dibromoindoline (430 mg, 1.55 mmol) at 140° C. for 4 h. The reaction mixture was dissolved in $CH_2Cl_2$ (6 mL), filtered and chromatographed on silica gel using 30% EtOAc/hexanes as eluent to give the product (0.25 g, 50% yield). Elemental analysis. Theory: C, 43.57; H, 04.06; N, 16.94; Found: C, 43.84; H, 3.87; N, 16.61.

EXAMPLE 288

Preparation of (R,S)-8—Chloro-1,2,3,4-tetrahydro-1-[1-[1-(methoxymethy)lpropyl]-6-methyl-1H-1,2,3-triazolo[4,5-c]pyridin-4-yl]-6-methylquinoline Synthesized by reaction of 8-Chloro-6-methyl-1,2,3,4-tetrhydroquinoline and 7-chloro-3-[1-(1-methoxymethyl)propyl]-5-methyl-3H-1,2,3-triazolo[4,5-d]-pyridine in the presence of NaHMDS as described in Example 1.

Elemental analysis. Theory: C, 63.07; H, 06.55; N, 17.51; Found: C, 62.98; H, 6.46; N, 17.15.

EXAMPLE 400

Preparation of N-(5,7-dibromo-2,3-dihydroindol-1-yl)-3,6-dimethyl-1-(1-ethylpropyl)]-1H-pyrazolo[3,4-d]pyrimidin-4-amine Part A:
3-Pentylhydrazine HCl:

In a 500 mL flask was placed 18.56 g (0.215 moles; fw 86.13; bp 102° C.) of 3-pentanone (Aldrich), 14.8 g (0.2 moles; fw 74) of acetylhydrazine (Aldrich) and 200 mL of absolute ethanol (Aldrich). The reaction mixture was refluxed for 18 h and then evaporated to dryness to afford 28.0 g of white crystalline solid. The crude hydrazone was dissolved in 200 ml of glacial AcOH (Baker) containing 1.0 g of $PtO_2$ (Aldrich) and hydrogenated at 50 PSI hydrogen pressure for 14 h. The catalyst from the mixture was filtered and evaporated to dryness to afford 37.34 g of colorless viscous oil. The oil was treated with 100 ml of water and acidified using 16 ml of con. HCl and extracted the aq. layer with 200 mL of diethyl ether to remove non basic compounds. The aq. layer was adjusted to PH 9 using solid $Na_2CO_3$ and extracted with diethyl ether (3*100 mL). The organic extract was concentrated to afford to give 20.9 g of acetylhydrazine derivative as a colorless oil. Acetylhydrazine derivative was dissolved in 100 mL of 12% aq. HCl (33 mL con. HCl+67 mL water) and refluxed for 3 h. The reaction mixture was evaporated to dryness to afford 22.4 g of 3-pentylhydrazine HCl as a white semi solid. NMR ($CDCl_3$) $\partial$ 1.0 (t, 6H, 2*$CH_3$), 1.8–2.0 (m, 4H, 2*$CH_2$), 3.4 (m, 1H, CH), 7.95–8.0 (bs, $NH_2$) and mass spectrum (M+H at 103). Over all yield 80.2%.

Part B:
5-Amino-4-cyano-[1-(1-ethylpropyl)]-3-methylpyrazole:

11.9 g of 3-pentylhydrazine hydrochloride (Part A), 11.7 g of 1-ethoxyethylidine malononitrile and 26.0 g of triethylamine were dissolved in 100 mL of methanol and refluxed for a period of 20 h. The solvent was stripped in vacuo and partitioned the residue with 100 mL each of water and ethyl acetate and extracted the aqueous layer with 2*50 mL of ethyl acetate. The combined organic extracts were washed with brine, dried and stripped in vacuo to afford 16.8 g of brown oil. The oil was purified by flash column chromatography (1:100 MeOH/dichloromethane eluent) to afford 11.7 g (71%) of desired pyrazole derivative as a white crystalline solid (mp. 117–118° C.). Anal. calcd. for $C_{10}H_{16}N_4$: C, 62.47; H, 8.40; N, 29.14. Found: C, 62.17; H, 8.39; N, 29.18.

Part C:
5-Amino-[1-(1-ethylpropyl)]-3-methylpyrazole-4-carboxamide:

8.0 g of the above nitrile (part B) was added to a ice cold stirred solution of concentrated sulfuric acid (20 mL) over 60 mins. After the addition the mixture was stirred at room temperature overnight. The reaction mixture was poured over 100 g of crushed ice and adjusted PH 8 to 9 using 50% NaOH solution. The mixture was extracted with ethyl acetate (3*75 mL), washed the organic extract with brine and dried. The solvent was stripped off and the pasty mass was crystallized from 2-propanol to afford 8.3 g(86% yield) of white crystalline solid (mp. 91–92° C.). Anal. calcd. for $C_{10}H_{18}N_4O$: C, 57.12; H, 8.64; N, 26.64. Found: C, 57.13; H, 8.51; N, 26.42.

Part D:
3,6-Dimethyl-[1-(1-ethyl-propyl)]-4-hydroxy-1H-pyrazolo[3,4-d]pyrimidine:

7.4 g of Part C material, 17.0 mL of ethyl acetate, 33.8 mL of 21% NaOEt were dissolved in 100 mL of ethanol and refluxed for a period of 24 h. The solvent from the reaction mixture was stripped off in vacuo and the residue was dissolved in 50 mL of water and acidified with concentrated hydrochloric acid to PH 5 to 6. The cream colored solid separated from the mixture was filtered and dried to afford 7.65 g of desired product (93.4%; mp. 202–203° C.). Anal. calcd. for $C_{12}H_{18}N_4O$: C, 61.52; H, 7.74; N, 23.91. Found: C, 61.23; H, 7.70; N, 23.62.

Part E:

4—Chloro-3,6-dimethyl-[1-(1-ethyl-propyl)]-1H-pyrazolo[3,4-d]pyrimidine:

The product of Part D (7.0 g) and 70 mL of phosphorous oxychloride were mixed and refluxed for a period of 6 h. Excess phosphorous oxychloride was stripped off in vacuo and the residue was poured over 50 g of ice. The resultant aqueous layer was extracted with 3*50 mL of ethyl acetate, washed the organic layer with brine (2*50 mL) and dried. The solvent was stripped off in vacuo and purified the crude by flash column chromatography (1:100 MeOH/dichloromethane) to afford 5.7 g (75%) of desired product as a cream colored solid (mp. 33–34° C.). Anal. calcd. for $C_{12}H_{17}N_4Cl$: C, 57.03; H, 6.79; N, 22.17. Found: C, 57.12; H, 6.70; N, 22.17.

Part F:

Title Compound: The product of part E (0.126 g) and 5,7-dibromoindoline (0.277 g) were heated together at 130° C. for 6 h under nitrogen atmosphere. The residue was then subjected to flash column chromatography (1:100 MeOH+dichloromethane) to yield an oil and it was crystallized from diethyl ether to give 0.077 g (31% yield) of desired product as a brown solid (mp. 190–191° C.). Anal. calcd. for $C_{20}H_{23}N_5Br_2$: C, 48.70; H, 4.70; N, 14.20. Found: C, 49.18; H, 4.72; N, 13.90.

EXAMPLE 500

Preparation of 4-(5,7-dimethoxy-2,3-dihydro-1H-indol-1-yl)-1-[1-ethylpropyl]-6-methyl-1H-1,2,3-triazolo[4,5-c]pyridine Part A:

To 5-methoxyindole (5.0 g) in glacial acetic acid (90 mL, 15–17° C.) was added sodium cyanoborohydride (6.41 g, 3 eq.), and the mixture was stirred 2 h. Water (250 mL) was added to the mixture, which was then cooled in an ice bath and made strongly basic with sodium hydroxide pellets. The solution was extracted with ether, which was then washed with water and brine and dried over $MgSO_4$. The ether solution was concentrated to give 5-methoxyindoline, which was reacted without further purification.

Part B:

5-Methoxyindoline and di-tert-butyl dicarbonate (8.95 g, 1.2 eq.) were stirred in THF overnight at room temperature. The solution was concentrated in vacuo and recrystallized from Et2O/hexane to give 1-(tert-Butoxycarbonyl)-5-methoxyindoline (6.25 g, 74% yield for two steps).

Part C:

To 1-(tert-Butoxycarbonyl)-5-methoxyindoline (2.0 g) and TMEDA (1.57 mL, 1.3 eq.) in ether (40 mL) at −78° C. was added sec-BuLi (7.4 mL, 1.2 eq.). The reaction was warmed to −40° C. for 2 hours and then cooled to −78° C. 1,2-dibromoethane (2.07 mL, 3 eq.) was added and the reaction stirred for 45 minutes at −78° C. The bath was then removed and the reaction was stirred for 1 hour. The reaction was quenched with water and extracted with ether. The ether was washed with brine, dried over $MgSO_4$, and concentrated. The crude product was chromatographed on silica gel, using hexane/ethyl acetate (19:1) as eluent, affording 1-(tert-butoxycarbonyl)-7-bromo-5-methoxyindoline (1.16 g).

Part D:

To 1-(tert-butoxycarbonyl)-7-bromo-5-methoxyindoline (1.16 g) in methanol (28 mL) was added HCl/ether (1.0 M, 14.1 mL, 4 eq.). The reaction was heated at 55° C. for 4 hours and then cooled to room temperature. Water (25 mL) was added and the pH was adjusted to 9 with NaOH (1 N, aq.). The mixture was extrated with ether, which was washed with brine, dried over $MgSO_4$, and concentrated to give 7-bromo-5-methoxyindoline (685 mg).

Part E:

To 7-bromo-5-methoxyindoline (382 mg) and 4-chloro-1-[1-ethylpropyl]-6-methyl-1H-1,2,3-triazolo[4,5-c]pyridine (400 mg) in THF (2.0 mL) was added sodium bis(trimethylsilyl)amide (1.0 M in THF, 15 mL) at 0° C. The reaction was warmed to ambient temperature and stirred for 1 hour. Ethyl acetate (150 mL) was added and washed with water and brine. The organics were dried over $MgSO_4$ and concentrated. The crude product was chromatographed on silica gel using ethyl acetate/hexane (1:4) as eluent to give 4-(7-bromo-5-methoxy-2,3-dihydro-1H-indol-1-yl)-1-(1-ethylpropyl)-6-methyl-1H-1,2,3-triazolo[4,5-c]pyridine (538 mg).

Part F:

To the product of part E (200 mg) in DMF (2.5 mL) was added cuprous bromide (7 mg) and sodium methoxide (25% w/w solution in methanol, 117 mL). The mixture was heated at reflux for 5 hours. The reaction was cooled and partitioned between ethyl acetate and water. The organic layer was washed with brine, dried over $MgSO_4$, and concentrated to give the title compound (128 mg). MS ($NH_3$—CI) m/z 382 (M+H)+.

EXAMPLE 501

Preparation of (R,S)-4-(5,7-dichloro-2,3-dihydro-1H-indol-1-yl)-1-[1-(cyanomethyl)propyl]-6-methyl-1H-1,2,3-triazolo[4,5-c]pyridine The title compound was prepared in a manner similar to the product of Example 500. Elemental analysis calcd. for $C_{19}H_{18}N_6Cl_2$: C, 56.87; H, 4.52; N, 20.94. Found: C, 56.50; H, 4.34; N, 20.58.

EXAMPLE 502

Preparation of (S)-4-(7-chloro-5-methoxy-2,3-dihydro-1H-indol-1-yl)-1-[1-(methoxymethyl)propyl]-6-methyl-1H-1,2,3-triazolo[4,5-c]pyridine The title compound was prepared in a manner similar to the product of Example 500.

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 $\mu$M hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 EN MgCl$_2$, 2 mM EGTA, 1 $\mu$g/l aprotinin, 1 $\mu$g/ml leupeptin and 1 $\mu$g/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 $\mu$g/ml to be used in the assay.

Binding assays are performed in 96 well plates; each well having a 300 $\mu$l capacity. To each well is added 50 $\mu$l of test drug dilutions (final concentration of drugs range from $10^{-10}$–$10^{-5}$ M), 100 $\mu$l of 125I -ovine-CRF ($^{125}$I-o-CRF) (final concentration 150 $\mu$M) and 150 $\mu$l of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a Ki value of less than about 10000 nM for the inhibition of CRF.
Inhibition of CRF-Stimulated Adenylate Cyclase Activity Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 mM oCRF, antagonist peptides (concentration range $10^{-9}$ to $10^{-6}$ m) and 0.8 mg original wet weight tissue (approximately 40–60 mg protein). Reactions are initiated by the addition of 1 mM ATP/$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 $\mu$l of [$^3$H]cAMP (approximately 40,000 dpm) is added to each tube prior to separation. The separation of [$^{32}$P]cAMP from [$^{32}$P]ATP is performed by sequential elution over Dowex and alumina columns.
In Vivo Biological Assay The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (I)

and isomers thereof, stereoisomeric forms thereof, or mixtures of stereoisomeric forms thereof, and pharmaceutically acceptable salt forms thereof wherein:

Q is selected from the group consisting of:

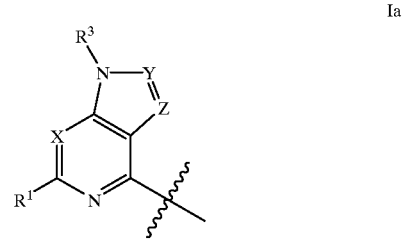

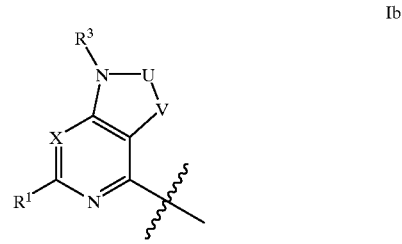

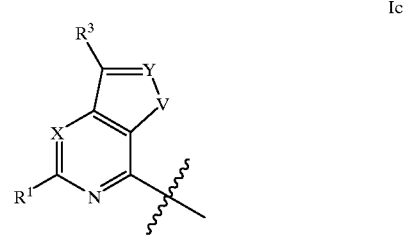

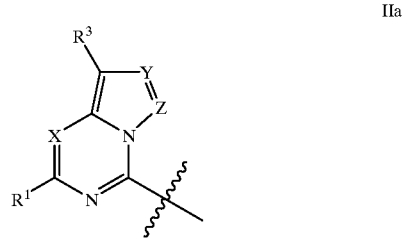

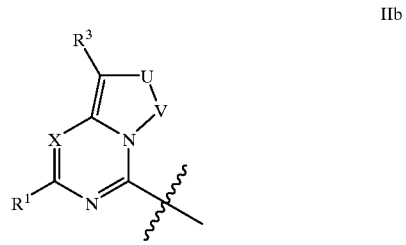

-continued

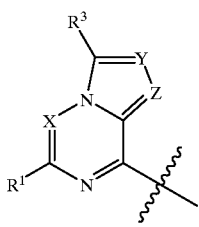

IIc

X is N or $CR^1$;
Y and Z are independently N or $CR^2$;
U and V are independently >C=G, $CR^{13}R^{14}$, $NR^{13}$, O, or S without forming O—O, S—O, or S—S bonds;
G is O or S;
$R^1$ is independently at each occurrence —H, halogen, —CN, $C_1$–$C_4$-haloalkyl, —$NR^9R^{10}$, —$NR^9COR^9$, —$COR^{10}$, —$OR^{10}$, SH, —$S(O)_nR^{12}$, $C_1$–$C_6$ alkyl, $C_2$–$C_6$ alkenyl, $C_2$–$C_6$ alkynyl, $C_3$–$C_6$ cycloalkyl, or $C_4$–$C_8$ cycloalkylalkyl, where each $C_1$–$C_6$ alkyl, $C_2$–$C_6$ alkenyl, $C_2$–$C_6$ alkynyl, $C_3$–$C_6$ cycloalkyl, and $C_4$–$C_8$ cycloalkylalkyl are optionally substituted with halogen, —CN, $C_1$–$C_4$ haloalkyl, —$NR^9R^{10}$, —$NR^9COR^9$, —$COR^{10}$, —$OR^{10}$, SH or —$S(O)_nR^{12}$;
$R^2$ is —H, halogen, —CN, $C_1$–$C_4$ haloalkyl, —$NR^9R^{10}$, —$NR^9COR^9$, —$COR^{10}$, —$OR^{10}$, SH, —$S(O)_nR^{12}$, $C_1$–$C_4$ alkyl, $C_3$–$C_6$ cycloalkyl or $C_3$–$C_7$ cycloalkylalkyl, where each $C_1$–$C_4$ alkyl, $C_3$–$C_6$ cycloalkyl, and $C_3$–$C_7$ cycloalkylalkyl are optionally substituted with halogen, CN, $C_1$–$C_4$ haloalkyl, —$NR^9R^{10}$, $NR^9COR^9$, —$COR^{10}$, —$OR^{10}$, SH or —$S(O)_nR^{12}$;
$R^3$ is $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_5$–$C_{10}$ cycloalkenylalkyl, where one carbon in any cycloalkyl ring may be replaced with O, S or $NR^9$ and each $C_1$–$C_{10}$ alkyl, $C_2$–$C_{10}$ alkenyl, $C_2$–$C_8$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_5$–$C_{10}$ cycloalkenylalkyl are optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, SH, —$S(O)_nR^{11}$, —$COR^6$, —$NHR^6SO_2R^8$, —$OC(O)NR^6R^7$, —$N_3$, —$OC(O)OR^7$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$CO_2H$, aryl, heteroaryl and heterocyclyl;
alternatively, R3 is —$OR^{3a}$, —$NR^{3a}R^{3a}$, —$NHR^{3a}$, —$SO_nR^{3a}$, —$SO_2NHR^{3a}$, —$SO_2NR^{3a}R^{3b}$, —$COR^{3a}$, —$CONHR^{3a}$, or $CONR^{3a}R^{3b}$;
$R^{3a}$ and $R^{3b}$ are independently $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, or $C_5$–$C_{10}$ cycloalkenylalkyl, where one carbon in any cycloalkyl may be replaced with O, S or $NR^9$ and each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, and $C_5$–$C_{10}$ cycloalkenylalkyl are optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, —SH, —$S(O)_nR_{11}$, —$COR^6$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$NHR^6SO_2R^8$, —$OC(O)NR^6R^7$, —$N_3$, —$OC(O)OR^7$, —$CONR^6R^7$, —$CO_2H$, aryl, heteroaryl and heterocyclyl;
L is $C(R^4)_2C(R^4)_2$ or $CR^4=CR^4$;
$R^4$ is independently selected in each occurrence from H, —$OR^{10}$, —$COR^9$, —$C_2$, $R^8$, —$CONR^9R^{10}$, —CN, —$NR^9R^{10}$, —$S(O)_nR^{12}$, halogen, $C_1$–$C_6$ alkyl, $C_1$–$C_4$ haloalkyl, $C_3$–$C_6$ cycloalkyl, $C_2$–$C_6$ alkenyl, $C_2$–$C_6$ alkynyl, aryl or heteroaryl, where in $C_1$–$C_6$ alkyl, $C_1$–$C_4$ haloalkyl, $C_3$–$C_6$ cycloalkyl, $C_2$–$C_6$ alkenyl, and $C_2$–$C_6$ alkynyl are optionally substituted with —$OR^{10}$, —$COR^9$, —$CO_2R^8$, —$CONR^9R]O$, —CN, —$NR^9R^{10}$, —$S(O)_nR^{12}$ or halogen;
$A^1$–$A^4$ are each $CR^5$;
$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6CO R^7$, —$NR^6CO_2R^8$, —$CO R^6$—$O R^7$, —$CONR^6R^7$, —$CO(NOR^9)R^{11}$, —$CO_2R^8$, or —$S(O)_n R^{11}$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with i to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, an d —$S(O)_nR^{11}$ and wherein two adjacent $R^5$ groups can form a 5–7 membered ring saturated or unsaturated optionally containing 1–2 O or SON or 1–3 N heteroatoms and optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO_2R^8$, —$CO(NOR^9)R^7$, or —$S(O)_n R^{11}$ and not containing any S—S, O—O, S—O or N—S bonds in the ring;
$R^6$ and $R^7$ are independently at each occurrence H, $C_1$–$C_6$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, $C_5$–$C_{12}$ bis(alkoxy)alkyl, aryl, aryl($C_1$–$C_4$ alkyl)-, heteroaryl, heteroaryl($C_1$–$C_4$ alkyl) or $NR^6R^7$ is piperidine, pyrrolidine, piperazine, N-methylpiperazine, morpholine or thiomorpholine;
$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl);
$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_2$–$C_6$ alkoxyalkyl, or $C_4$–$C_7$ cycloalkylalkyl;
$R^{11}$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl, heteroaryl($C_1$–$C_4$ alkyl), or —$NR^6R^7$;
$R^{12}$ is independently at each occurrence $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, or $C_4$–$C_7$ cycloalkylalkyl;
$R^{13}$ and $R^{14}$, are independently at each occurrence H, $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl, heteroaryl($C_1$–$C_4$ alkyl)-, —$COR^{12}$, —$CO_2R^8$, —$CONR^9$, or $S(O)_nR^{12}$;

aryl is phenyl or naphthyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, —SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, —SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

heterocyclyl is saturated or partially saturated heteroaryl, optionally substituted with 1 to 3 substituents independently selected at each occurrence from $C_1$–$C_6$ alkyl, $C_3$–$C_6$-cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^{12}$, —$OC(O)R^{12}$, —$NR^9COR^9$, —$N(COR^{12})_2$, —$NR^9CONR^9R^{10}$, —$NR^9CO_2R^{12}$, —$NR^9R^{10}$, and —$CONR^9R^{10}$;

n is independently at each occurrence 0, 1 or 2;
provided that:
(a) when Q is $I_a$, $I_b$ or $I_c$ and X is N, $R^1$ is other than H and $CH_3$;
(b) $R^1$ is other than O-alkynyl or S-alkynyl; and
(c) when Q is $I_b$, X is N, U is $CR^{13}R^{14}$, and V is $CR^{13}R^{14}$, then $R^1$ is other than $NR^9R^{10}$.

2. A compound of claim 1 and isomers thereof, stereoisomeric forms thereof, or mixtures of stereoisomeric forms thereof, and pharmaceutically acceptable salt forms thereof wherein, independently or concurrently:

Q is Ia, Ib, Ic;

X is N or $CR^1$;

Y, Z are independently N or $CR^2$;

U, V are >C=G, $CR^{13}R^{14}$, or $NR^{13}$, O, or S without forming O—O, S—O, or S—S bonds;

G is O;

$R^1$ is independently at each occurrence H, $C_1$–$C_4$alkyl, $C_3$–$C_6$cycloalkyl, halogen, —CN, —$NR^9R^{10}$, —$NR^9COR^{10}$, $C_1$–$C_4$ haloalkyl, —$COR^{10}$, —$OR^{10}$ or —$S(O)_nR^{12}$;

$R^2$ is independently at each occurrence —H, $C_1$–$C_4$alkyl, $C_3$–$C_6$cycloalkyl, halogen, —CN, —$NR^9R^{10}$, —$NR^9COR^{10}$, $C_1$–$C_4$ haloalkyl, —$COR^{10}$, —$OR^{10}$ or —$S(O)_nR^{12}$;

$R^3$ is $C_1$–$C_{10}$ alkyl, $C_2$–$C_{10}$ alkenyl, $C_2$–$C_{10}$ alkynyl, $C_3$–$C_8$cycloalkyl, $C_4$–$C_{12}$cycloalkylalkyl, $C_2$–$C_{10}$ alkoxyalkyl, $C_5$–$C_{10}$ cycloalkenyl, $C_5$–$C_{10}$ cycloalkenylalkyl, where one carbon in any cycloalkyl may be replaced with O, S or $NR^9$ and each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$cycloalkylalkyl, $C_2$–$C_{10}$ alkoxyalkyl, $C_5$–$C_{10}$ cycloalkenyl, $C_5$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halo, $C_1$–$C_4$ haloalkyl, cyano, —$OR^7$, SH, —$S(O)_nR^{11}$, —$COR^6$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$NHR^6SO_2R^8$, —$OC(O)NR^6R^7$, —$N_3$, —$OC(O)OR^7$, —$CO_2H$, aryl, heteroaryl and heterocyclyl;

$R^4$ is independently selected in each occurrence —H, —$OR^{10}$, —$COR^9$, —$CO_2R^8$, —$CONR^9R^{10}$, —CN, —$NR^9R^{10}$, —$S(O)_nR^{12}$, halogen, $C_1$–$C_6$ alkyl, $C_1$–$C_4$ haloalkyl, $C_3$–$C_6$ cycloalkyl, $C_2$–$C_6$ alkenyl, $C_2$–$C_6$ alkynyl, aryl or heteroaryl, each optionally substituted with the following functional groups: —$OR^{10}$, —$COR^9$, $CO_2R^8$, —$CONR^9R^{10}$, —CN, —$NR^9R^{10}$, —$S(O)_nR^{12}$, halogen, or two $R^4$ taken together form one or two carbonyl(s) or thiocarbonyl(s);

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$ cycloalkylalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO(NOR^9)R^{11}$, —$CO_2R^8$, or —$S(O)_nR^{11}$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, $NR^6CO_2R^8$, —$COR^6$—$OR^7$, —$CONR^6R^7$, —$CO_2R^8$, —$CO(NOR^9)R^7$, or —$S(O)_nR^{11}$ and wherein two adjacent $R^5$ groups can form a 5–7 membered ring saturated on unsaturated optionally containing 1–2 O or $SO_n$ or 1–3 N heteroatoms optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, $NR^6COR^7$, $NR^6CO_2R^8$,—$COR^6$,—$OR^7$,—$CONR^6R^7$,—$CO_2R^8$, —$CO(NOR^9)R^7$, or —$S(O)_nR^{11}$ and not containing any S—S, O—O, S—O or N—S bonds in the ring;

$R^6$ and $R^7$ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl); $R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^{11}$ is $C_1$–$C_4$ alkyl, $C_1$–$C_4$ haloalkyl, $C_2$–$C_8$ alkoxyalkyl, $C_3$–$C_6$cycloalkyl, $C_4$–$C_{12}$cycloalkylalkyl, aryl, aryl ($C_1$–$C_4$ alkyl), heteroaryl or heteroaryl($C_1$–$C_4$ alkyl), piperidine, pyrrolidine, piperazine, N-methylpiperazine, morpholine or thiomorpholine;

$R^{12}$ is $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^{13}$ and $R^{14}$ are independently H, $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl)-, —$COR^{12}$, —$CO_2R^8$, —$CONR^9$, —$S(O)_nR^{12}$;

aryl is phenyl or naphthyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_n$ $R^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

n is independently at each occurrence 0, 1 or 2.

3. A compound of claim 1 and isomers thereof, stereoisomeric forms thereof, or mixtures of stereoisomeric forms thereof, and pharmaceutically acceptable salt forms thereof wherein, independently or concurrently:

Q is IIa, IIb, or IIc;

X is N or $CR^1$;

Y, Z are independently N or $CR^2$;

U, V are >C=G, $CR^{13}R^{14}$, or $NR^{13}$, O, or S without forming O—O, S—O, or S—S bonds;

G is O;

$R^1$ is independently at each occurrence H, $C_1$–$C_4$ alkyl, $C_3$–$C_6$ cycloalkyl, halogen, —CN, —$NR^9R^{10}$, —$NR^9COR^{10}$, $C_1$–$C_4$ haloalkyl, —$COR^{10}$, —$OR^{10}$ or —$S(O)_nR^{12}$;

$R^2$ is independently at each occurrence H, $C_1$–$C_4$ alkyl, $C_3$–$C_6$ cycloalkyl, halogen, —CN, —$NR^9R^{10}$, —$NR^9COR^{10}$, $C_1$–$C_4$ haloalkyl, —$COR^{10}$, —$OR^{10}$ or —$S(O)_nR^{12}$;

$R^3$ is $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, $C_5$–$C_{10}$ cycloalkenylalkyl, where one carbon in any cycloalkyl may be replaced with O, S or $NR^9$ and each $C_1$–$C_{10}$ alkyl, $C_2$–$C_{10}$ alkenyl, $C_2$–$C_{10}$ alkynyl, $C_3$–$C_8$ cycloalkyl, $C_4$–$C_{12}$ cycloalkylalkyl, $C_2$–$C_{10}$ alkoxyalkyl, $C_5$–$C_{10}$ cycloalkenyl, $C_5$–$C_{10}$ cycloalkenylalkyl is optionally substituted with 1 to 3 substituents independently selected at each occurrence from $C_1$–$C_6$ alkyl, $C_2$–$C_6$ alkenyl, $C_2$–$C_{10}$ alkynyl, $C_3$–$C_6$ cycloalkyl, halogen, $C_1$–$C_4$ haloalkyl, cyano, —$OR^7$, SH, —$S(O)_nR^{11}$, —$COR^6$, —$CO_2R^8$, —$OC(O)R^6$, —$NR^7COR^6$, —$N(COR^6)_2$, —$NR^7CONR^6R^7$, —$NR^7CO_2R^8$, —$NR^6R^7$, —$CONR^6R^7$, —$NHR^6SO_2R^8$, —$OC(O)NR^6R^7$, —$N_3$, —$OC(O)OR^7$, —$CO_2H$, aryl, heteroaryl and heterocyclyl;

$R^4$ is independently selected in each occurrence —H, —$OR^{10}$, —$COR^9$, —$CO_2R^8$, —$CONR^9R^{10}$, —CN, —$NR^9R^{10}$, —$S(O)_nR^{12}$, halogen, $C_1$–$C_6$ alkyl, $C_1$–$C_4$ haloalkyl, $C_3$–$C_6$ cycloalkyl, $C_2$–$C_6$ alkenyl, $C_2$–$C_6$ alkynyl, aryl or heteroaryl, each optionally substituted with the following functional groups: —$OR^{10}$, —$COR^9$, $CO_2R^8$, —$CONR^9R^{10}$, —CN, —$NR^9R^{10}$, —$S(O)_nR^{12}$, halogen, or two $R^4$ taken together form one or two carbonyl(s) or thiocarbonyl(s);

$R^5$ is independently at each occurrence —H, $C_1$–$C_{10}$ alkyl, $C_1$–$C_4$ haloalkyl, $C_1$–$C_4$ haloalkoxy, $C_2$–$C_{10}$ alkenyl, $C_2$–$C_{10}$ alkynyl, $C_3$–$C_6$ cycloalkyl, $C_4$–$C_{12}$cycloalkylalkyl, —$NO_2$, halogen, —CN, —$NR^6R^7$, —$NR^6COR^7$, —$NR^6CO_2R^8$, —$COR^6$— $OR^7$, —$CONR^6R^7$, —$CO(NOR^9)R^{11}$, —$CO_2R^8$, or —$S(O)_nR^{11}$, where $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $C_2$–$C_4$ alkenyl, $C_2$–$C_4$ alkynyl, $C_3$–$C_6$ cycloalkyl, $C_4$–$C_8$ cycloalkylalkyl, $C_1$–$C_4$ haloalkyl, —$NO_2$, halogen, —CN, —$NR^6R^7$, —$NR^6COR^7$, —$NR^6CO_2R^8$, —$COR^6$—$OR^7$, —$CONR^6R^7$, —$CO_2R^8$, —$CO(NOR^9)R^7$, or —$S(O)_nR^{11}$ and wherein two adjacent $R^5$ groups can form a 5–7 membered ring saturated on unsaturated optionally containing 1–2 O or $SO_n$ or 1–3 N heteroatoms optionally substituted with $C_1$–$C_4$ alkyl, $C_2$–$C_6$ alkenyl, $C_2$–$C_6$ alkynyl, $C_3$–$C_6$ cycloalkyl, $C_4$–$C_8$cycloalkylalkyl, $C_1$–$C_4$ haloalkyl, —$NO_2$, halogen, —CN, —$NR^6R^7$, $NR^6COR^7$, $NR^6CO_2R^8$, —$COR^6$, —$OR^7$, —$CONR^6R^7$, —$CO_2R^8$, —$CO(NOR^9)R^7$, or —$S(O)_nR^{11}$ and not containing any S—S, O—O, S—O or N—S bonds in the ring;

$R^6$ and $R^7$ are independently at each occurrence H, $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-; or $NR^6R^7$ is piperidine, pyrrolidine, piperazine, N-methylpiperazine, morpholine or thiomorpholine;

$R^8$ is independently at each occurrence $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl), heteroaryl or heteroaryl($C_1$–$C_4$ alkyl);

$R^9$ and $R^{10}$ are independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^{11}$ is $C_1$–$C_4$ alkyl, $C_1$–$C_4$ haloalkyl, $C_2$–$C_8$ alkoxyalkyl, $C_3$–$C_6$cycloalkyl, $C_4$–$C_{12}$cycloalkylalkyl, aryl, aryl($C_1$–$C_4$ alkyl)-, heteroaryl or heteroaryl($C_1$–$C_4$ alkyl), piperidine, pyrrolidine, piperazine, N-methylpiperazine, morpholine or thiomorpholine;

$R^{12}$ is $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, $C_4$–$C_7$ cycloalkylalkyl;

$R^{13}$ and $R^{14}$ are independently H, $C_1$–$C_4$ alkyl, $C_1$–$C_4$ haloalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-, —$COR^{12}$, —$CO_2R^8$, —$CONR^9$, —$S(O)_nR^{12}$;

aryl is phenyl or naphthyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_n R^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

heteroaryl is pyridyl, pyrimidinyl, pyrazinyl, pyrdazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

heterocyclyl is saturated or partially saturated heteroaryl, optionally substituted with 1 to 3 substituents independently selected at each occurrence from $C_1$–$C_6$ alkyl, $C_3$–$C_6$ cycloalkyl, $C_4$–$C_7$ cycloalkylalkyl, $C_2$–$C_6$ alkenyl, $C_2$–$C_6$ alkynyl, halogen, $C_1$–$C_4$ haloalkyl, cyano, —$OR^{10}$, SH, —$S(O)_nR^{12}$, —$COR^{12}$, —$CO_2R^8$, —$OC(O)R^{12}$, —$NR^9COR^9$, —$N(COR^{12})_2$, —$NR^9CONR^9R^{10}$, —$NR^9CO_2R^8$, —$NR^9R^{10}$, and —$CONR^9R^{10}$;

n is independently at each occurrence 0, 1 or 2.

4. A compound of claim 1 and isomers thereof, stereoisomeric forms thereof, or mixtures of stereoisomeric forms thereof, and pharmaceutically acceptable salt forms thereof wherein Q is Ia and X is N.

5. A compound of claim 4 and isomers thereof, stereoisomeric forms thereof, or mixtures of stereoisomeric forms thereof, and pharmaceutically acceptable salt forms thereof wherein:

$R^1$ is selected independently at each occurrence from —Me, —Et, halogen, —CN, —$CF_3$, —OMe, —NHMe, —$NMe_2$, —COMe, —SOMe, and —$SO_2Me$; and $R^2$ is —H, —Me, halogen.

6. A compound of claim 4 and isomers thereof, stereoisomeric forms thereof, or mixtures of stereoisomeric forms thereof, and pharmaceutically acceptable salt or pro-drug forms thereof wherein:

Y and Z are N;

$R^1$ is —Me or halogen;

$R^2$ is —H, —Me, halogen;

$R^5$ is selected independently at each occurrence from H, $C_1$–$C_6$ alkyl, $C_1$–$C_4$ haloalkyl, $C_2$–$C_6$ alkenyl, $C_2$–$C_6$ alkynyl, $C_3$–$C_6$ cycloalkyl, $C_4$–$C_8$ cycloalkylalkyl, $C_1$–$C_4$ alkoxy, —$NO_2$, halogen, —CN, $C_1$–$C_4$ haloalkyl, —$NR^6R^7$, —$NR^6COR^7$, —$NR^6CO_2R^8$, —$COR^{11}$, —$OR^7$, —$CONR^6R^7$, —$CO(NOR^9)R^{11}$, —$CO_2R^8$, or —$S(O)_nR^{11}$;

$R^6$, $R^7$, and $R^9$ are selected independently at each occurrence selected from H, $C_1$–$C_4$ alkyl, $C_1$–$C_4$ haloalkyl, $C_3$–$C_6$ alkenyl, $C_3$–$C_6$ alkynyl, $C_3$–$C_6$ cycloalkyl, and $C_4$–$C_7$ cycloalkylalkyl; and $R^8$, and $R^{11}$ are selected independently at each occurrence from $C_1$–$C_4$ alkyl, $C_1$–$C_4$ haloalkyl, $C_3$–$C_6$ cycloalkyl, and $C_4$–$C_8$ cycloalkylalkyl.

7. A compound of claim 4 and isomers thereof, stereoisomeric forms thereof, or mixtures of stereoisomeric forms thereof, and pharmaceutically acceptable salt forms thereof, selected from the group consisting of:

(R,S)-4-(5,7-dibromo-2,3-dihydro-1H-indol-1-yl)-1-[1-methoxyethyl)propyl]-6-methyl-1H-1,2,3-triazolo[4,5-c] pyrimidine;

(R,S)-4-(5,7-dichloro-2,3-dihydro-4-indol-1-yl)-1-[1-methoxyethyl)propyl]-6-methyl-1H-1,2,3-triazolo[4,5-c] pyrimidine;

4-(7-chloro-5-methylsulfonyl-2,3-dihydro-4-indol-1-yl)-1-[1-methoxyethyl)propyl]-6-methyl-1H-1,2,3-triazolo [4,5-c] pyrimidine;

4-(7-chloro-5-methoxy-2,3-dihydro-4-indol-1-yl)-1-[1-methoxyethyl)propyl]-6-methyl-1H-1,2,3-triazolo[4,5-c] pyrimidine;

4-(7-chloro-5-methyl-2,3-dihydro-4-indol-1-yl)-1-[1-methoxyethyl)propyl]-6-methyl-1H-1,2,3-triazolo[4,5-c] pyrimidine;

4-(7-chloro-5-ethyl-2,3-dihydro-4-indol-1-yl)-1-(1-methoxyethyl)propyl]-6-methyl-1H-1,2,3-triazolo[4,5-c] pyrimidine;

4-(7-chloro-5-cyano-2,3-dihydro-4-indol-1-yl)-1-[1-methoxyethyl)propyl]-6-methyl-1H-1,2,3-triazolo[4,5-c] pyrimidine;

4-(5-acetyl-7-chloro-2,3-dihydro-4-indol-1-yl)-1-[1-methoxyethyl)propyl]-6-methyl-1H-1,2,3-triazolo[4,5-c] pyrimidine;

4-(7-chloro-5-thiomethyl-2,3-dihydro-4-indol-1-yl)-1-[1-methoxyethyl)propyl]-6-methyl-1H-1,2,3-triazolo[4,5-c] pyrimidine; and 4-(7-chloro-5-methylsulfonyl-2,3-dihydro-4-indol-1-yl)-1-[1-methoxyethyl)propyl]-6-methyl-1H-1,2,3-triazolo [4,5-c] pyrimidine.

8. A compound of claim 1 and isomers thereof, stereoisomeric forms thereof, or mixtures of stereoisomeric forms thereof, and pharmaceutically acceptable salt forms thereof wherein Q is Ia and X is $CR^1$.

9. A compound of claim 8 and isomers thereof, stereoisomeric forms thereof, or mixtures of stereoisomeric forms thereof, and pharmaceutically acceptable salt forms thereof, selected from the group consisting of:

(S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyridine;

(R,S)-4-(5,7-dibromo-2,3-dihydro-1H-indol-1-yl)-1-[1-(methoxymethyl)-3-methoxypropyl]-6-methyl-1H-1,2,3-triazolo[4,5-c]pyrdine;

(R,S)-4-(5,7-dibromo-2,3-dihydro-1H-indol-1-yl)-1-[1-(methoxymethyl)propyl]-6-methyl-1H-1,2,3-triazolo[4,5-c]pyridine;

4-(5,7-dimethoxy-2,3-dihydro-1H-indol-1-yl)-1-[1-ethylpropyl]-6-methyl-1H-1,2,3-triazolo[4,5-c] pyridine;

(R,S)-4-(5-bromo-7-methoxy-2,3-dihydro-1H-indol-1-yl)-1-[1-(methoxymethyl)propyl]-6-methyl-1H-1,2,3-triazolo[4,5-c]pyridine;

(R,S)-4-(5-bromo-7-methoxy-2,3-dihydro-1H-indol-1-yl)-1-[1-(methoxymethyl)-3-methoxypropyl]-6-methyl-1H-1,2,3-triazolo[4,5-c]pyridine;

(R,S)-4-(5-bromo-7-methyl-2,3-dihydro-1H-indolyl)-1-[1-(methoxymethy)lpropyl]-6-methyl-1H-1,2,3-triazolo[4,5-c] pyridine;

(R,S)-4-(5-bromo-7-chloro-2,3-dihydro-1H-indol-1-yl)-1-[1-methoxymethyl)propyl]-6-methyl-1H-1,2,3-triazolo[4,5-c]pyridine;

(R,S)-4-(5-bromo-7-chloro-2,3-dihydro-1H-indol-1-yl)-1-[1-(methoxymethyl)-3-methoxypropyl]6-methyl-1H-1,2,3-triazolo[4,5-c]pyridine;

(R,S)-4-(7-chloro-5-methoxy-2,3-dihydro-1H-indol-1-yl)-1-[1-(methoxymethyl)-3-methoxypropyl]-6-methyl-1H-1,2,3-triazolo[4,5-c]pyridine;

(S)-4-(7-chloro-5-methoxy-2,3-dihydro-1H-indol-1-yl)-1-[1-(methoxymethyl)propyl]-6-methyl-1H-1,2,3-triazolo[4,5-c]pyridine;

(R,S)4-(7-chloro-5-methyl-2,3-dihydro-1H-indol-1-yl)-1-[1-(methoxymethyl)-3-methoxypropyl)-6-methyl-1H-1,2,3-triazolo[4,5-c]pyridine;

(R,S)-4-(7-chloro-5-ethyl-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-cyano-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-thiomethyl-2,3-dihydro-1H-indol-1-yl)-1-[1-(methoxymethyl)-3-methoxypropyl]-6-methyl-1H-1,2,3-triazolo[4,5-c]pyridine;

(R,S)-4-(7-chloro-5-methoxy-2,3-dihydro-1H-indol-1-yl)-1-fi -(methoxymethy)propyl]-6-methyl-1H-1,2,3-triazolo[4,5-c]pyridine;

(R,S)-4-(7-chloro-5-methyl-2,3-dihydro-1H-indol-1-yl)-1-[1-(methoxymethy)propyl]-6-methyl-1H-1,2,3-triazolo[4,5-c]pyridine;

(R,S)-4-(7-chloro-5-ethyl-2,3-dihydro-1H-indol-1-yl)-1-[1-(methoxymethy)propyl]-6-methyl-1H-1,2,3-triazolo[4,5-c]pyridine;

(R,S)-4-(7-chloro-5-cyano-2,3-dihydro-1H-indol-1-yl)-1-[1-(methoxymethy)propyl]-6-methyl-1H-1,2,3-triazolo[4,5-c]pyridine;

4-(7-chloro-5-thiomethyl-2,3-dihydro-1H-indol-1-yl)-1-(1-ethylpropyl)-6-methyl-1H-1,2,3-triazolo[4,5-c]pyridine;

4-(7-chloro-5-methylsulfonyl-2,3-dihydro-1H-indol-1-yl)-1-(1-ethylpropyl)-6-methyl-1H-1,2,3-triazolo[4,5-c]pyridine;

4-(7-chloro-5-methoxy-2,3-dihydro-1H-indol-1-yl)-1-(1-ethylpropyl)-6-methyl-1H-1,2,3-triazolo[4,5-c]pyridine;

4-(7-chloro-5-methyl-2,3-dihydro-1H-indol-1-yl)-1-(1-ethylpropyl)-6-methyl-1H-1,2,3-triazolo[4,5-c]pyridine;

4-(7-chloro-5-ethyl-2,3-dihydro-1H-indol-1-yl)-1-(1-ethylpropyl)-6-methyl-1H-1,2,3-triazolo[4,5-c] pyrdine;

4-(7-chloro-5-cyano-2,3-dihydro-1H-indol-1-yl)-1-(1-ethylpropyl)-6-methyl-1H-1,2,3-triazolo[4,5-c]pyridine;

4-(5-acetyl-7-chloro-2,3-dihydro-1H-indol-1-yl)-1-(1-ethylpropyl)-6-methyl-1H-1,2,3-triazolo[4,5-c]pyridine;

4-(7-chloro-5-methylsulfonyl-2,3-dihydro-1H-indol-1-yl)-1-(1-ethylpropyl)-6-methyl-1H-1,2,3-triazolo[4,5-c]pyridine;

4-(5,7-dichloro-2,3-dihydro-1H-indol-1-yl)-1-(1-ethylpropyl)-6-methyl-1H-1,2,3-triazolo[4,5-c]pyridine;

(R,S)-4-(5,7-dichloro-2,3-dihydro-1H-indol-1-yl)-1-[1-(methoxymethyl)propyl]-6-methyl-1H-1,2,3-triazolo[4,5-c]pyridine;

(R,S)-4-(5,7-dichloro-2,3-dihydro-1H-indol-1-yl)-1-[1-(methoxymethyl)-3-methoxypropyl]-6-methyl-1H-1,2,3-triazolo[4,5-c]pyridine;

4-(5,7-dichloro-2,3-dihydro-1H-indol-1-yl)-1-[1-(methoxyethyl)-3-methoxypropyl]-6-methyl-1H-1,2,3-triazolo[4,5-c]pyridine;

(R,S)-4-(5,7-dichloro-2,3-dihydro-1H-indol-1-yl)-1-[1-(cyanomethyl)propyl]-6-methyl-1H-1,2,3-triazolo[4,5-c]pyridine;

N-(7-chloro-5-methoxy-1H-indol-1-yl)-1-(1-ethylpropyl)-6-methyl-1H-1,2,3-triazolo[4,5-c]pyridine;

N-(7-chloro-5-methyl-1H-indol-1-yl)-1-(1-ethylpropyl)-6-methyl-1H-1,2,3-triazolo[4,5-c]pyridine;

N-(7-chloro-5-ethyl-1H-indol-1-yl)-1-(1-ethylpropyl)-6-methyl-1H-1,2,3-triazolo[4,5-c]pyridine;

N-(7-chloro-5-cyano-1H-indol-1-yl)-1-(1-ethylpropyl)-6-methyl-1H-1,2,3-triazolo[4,5-c]pyridine;

N-(5-acetyl-7-chloro-1H-indol-1-yl)-1-(1-ethylpropyl)-6-methyl-1H-1,2,3-triazolo[4,5-c]pyridine;

N-(7-chloro-5-thiomethyl-1H-indol-1-yl)-1-(1-ethylpropyl)-6-methyl-1H-1,2,3-triazolo[4,5-c]pyridine; and N-(7-chloro-5-methylsulfony-1H-indol-1-yl)-1-(1-ethylpropyl)-6-methyl-1H-1,2,3-triazolo[4,5-c]pyridine.

10. A pharmaceutical composition comprising a pharmaceutically acceptable carrier and a therapeutically effective amount of a compound of claim 1.

11. A pharmaceutical composition comprising a pharmaceutically acceptable carrier and a therapeutically effective amount of a compound of claim 7.

12. A pharmaceutical composition comprising a pharmaceutically acceptable carrier and a therapeutically effective amount of a compound of claim 9.

13. A method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals, comprising: administering to the mammal a therapeutically effective amount of a compound of claim 1.

14. A method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of claim 7.

15. A method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of claim 9.

* * * * *